US011746343B2

(12) United States Patent
Konzak

(10) Patent No.: US 11,746,343 B2
(45) Date of Patent: Sep. 5, 2023

(54) WHEAT PLANTS HAVING INCREASED RESISTANCE TO IMIDAZOLINONE HERBICIDES

(71) Applicant: Northwest Plant Breeding Company, Pullman, WA (US)

(72) Inventor: Calvin Konzak, Pullman, WA (US)

(73) Assignee: Northwest Plant Breeding Company, Pullman, WA (US)

( * ) Notice: Subject to any disclaimer, the term of this patent is extended or adjusted under 35 U.S.C. 154(b) by 46 days.

(21) Appl. No.: 15/843,421

(22) Filed: Dec. 15, 2017

(65) Prior Publication Data

US 2018/0119129 A1 May 3, 2018

Related U.S. Application Data

(60) Continuation of application No. 15/290,128, filed on Oct. 11, 2016, which is a continuation of application No. 13/784,037, filed on Mar. 4, 2013, now abandoned, which is a division of application No. 12/362,935, filed on Jan. 30, 2009, now Pat. No. 8,389,809, which is a division of application No. 10/486,595, filed as application No. PCT/US02/21753 on Jul. 10, 2002, now Pat. No. 7,528,297.

(60) Provisional application No. 60/311,141, filed on Aug. 9, 2001.

(51) Int. Cl.
| C12N 9/88 | (2006.01) |
| C12N 15/82 | (2006.01) |
| A01H 6/46 | (2018.01) |
| A01H 5/10 | (2018.01) |
| A01N 43/50 | (2006.01) |
| C12Q 1/6895 | (2018.01) |

(52) U.S. Cl.
CPC .............. *C12N 9/88* (2013.01); *A01H 5/10* (2013.01); *A01H 6/4678* (2018.05); *A01N 43/50* (2013.01); *C12N 15/8274* (2013.01); *C12N 15/8278* (2013.01); *C12Q 1/6895* (2013.01); *C12Y 401/03* (2013.01); *C12Q 2600/13* (2013.01); *C12Q 2600/156* (2013.01); *C12Q 2600/158* (2013.01)

(58) Field of Classification Search
CPC ................... A01H 1/06; C12N 9/1022
See application file for complete search history.

(56) References Cited

U.S. PATENT DOCUMENTS

| 4,761,373 A | 8/1988 | Anderson et al. |
| 5,013,659 A | 5/1991 | Bedbrook et al. |
| 5,304,732 A | 4/1994 | Anderson et al. |
| 5,331,107 A | 7/1994 | Anderson et al. |
| 5,731,180 A * | 3/1998 | Dietrich ............. C12N 15/8278 800/278 |
| 5,767,361 A * | 6/1998 | Dietrich .................... C12N 9/88 800/300 |
| 5,853,973 A | 12/1998 | Kakefuda et al. |
| 5,928,937 A | 7/1999 | Kakefuda et al. |
| 6,211,438 B1 | 4/2001 | Anderson et al. |
| 6,211,439 B1 | 4/2001 | Anderson et al. |
| 6,222,100 B1 | 4/2001 | Anderson et al. |
| 6,225,105 B1 | 5/2001 | Sathasivan et al. |
| 6,339,184 B1 * | 1/2002 | Smith ...................... A01H 1/02 800/276 |
| 6,613,963 B1 * | 9/2003 | Gingera ................... A01H 5/00 435/418 |
| 6,696,294 B1 | 2/2004 | Konzak |
| 7,034,208 B1 * | 4/2006 | Smith ...................... A01H 1/06 800/276 |
| 7,250,561 B1 | 7/2007 | Pallett et al. |
| 7,528,297 B2 * | 5/2009 | Konzak .................... C12N 9/88 800/300 |
| 8,389,809 B2 * | 3/2013 | Konzak .................... C12N 9/88 800/300 |
| 9,499,833 B2 * | 11/2016 | Konzak .................... C12N 9/88 |
| 2003/0236208 A1 | 12/2003 | Kmeic et al. |

FOREIGN PATENT DOCUMENTS

| EP | 0360750 A2 | 3/1990 |
| EP | 0375875 | 7/1990 |
| EP | 0508161 A1 | 10/1992 |
| EP | 0525384 A2 | 2/1993 |
| WO | WO 90/14000 A1 | 11/1990 |
| WO | WO 99/65292 | 12/1999 |
| WO | WO 00/53763 | 9/2000 |
| WO | WO 01/85970 | 11/2001 |
| WO | WO 02/092820 A1 | 11/2002 |
| WO | WO 03/014356 A2 | 2/2003 |
| WO | WO 03/014357 | 2/2003 |
| WO | WO 03/014357 A1 | 2/2003 |

OTHER PUBLICATIONS

Wright et al Weed Science vol. 46, pp. 13-23 (Year: 1998).*
Newhouse et al Plant Physiology vol. 100 pp. 882-886 (Year: 1992).*
Wang et al May-Jun. 2001 Weed Science vol. 49 pp. 340-345 (Year: 2001).*
Seefeldt et al Weed Science vol. 46 pp. 632-634 (Year: 1998).*
J. Andrew Kendig and M.S. DeFelice, "ALS Resistance Cocklebur (*Xanthium strumarium* L.) in Missouri", WSSA Abstracts, vol. 34, Feb. 7-10, 1994, 1994 Meeting of the Weed Science Society of America.
Barrett, M., "Protection of Grass Crops from Sulfonylurea and Imidazolinone Toxicity," Crop Safeners for Herbicides, 1989, pp. 195-220, Academic Press, Inc.

(Continued)

*Primary Examiner* — David H Kruse
(74) *Attorney, Agent, or Firm* — Lowenstein Sandler LLP

(57) ABSTRACT

The present invention is directed to barley plants having increased resistance to an imidazolinone herbicide. The present invention also includes seeds produced by these barley plants and methods of controlling weeds in the vicinity of these barley plants.

17 Claims, 4 Drawing Sheets

Specification includes a Sequence Listing.

(56) References Cited

OTHER PUBLICATIONS

Bernasconi, P., et al., "A Naturally Occurring Point Mutation Confers Broad Range Tolerance to Herbicides That Target Acetolactate Synthase," The Journal of Biological Chemistry, 1995, pp. 17381-17385, vol. 270(29).

Brown, M., et al., "Hydrolytic Activation versus Oxidative Degradation of Assert Herbicide, an Imidazolinone Aryl-carboxylate, in Susceptible Wild Oat versus Tolerant Corn and Wheat," Pesticide Biochemistry and Physiology, 1987, pp. 24-29, vol. 27, Academic Press, Inc.

Chang, A., and R. Duggelby, "Herbicide-resistant Forms of *Arabidopsis thaliana* Acetohydroxyacid Synthase: Characterization of the Catalytic Properties and Sensitivity to Inhibitors of Four Defined Mutants," Biochemistry 1, 1998, pp. 765-777, vol. 333.

Chong C., and J. Choi, "Amino Acid Residues Conferring Herbicide Tolerance in Tobacco Acetolactate Synthase," Biochemical and Biophysical Research Communications, 2000, pp. 462-467, vol. 279, Academic Press.

Duggleby, R., et al., "Systematic Characterization of Mutations in Yeast Acetohydroxyacid Synthase," Eur. J Biochem., 2003, pp. 2895-2904, vol. 270.

Hattori, J., et al., "Multiple Resistance to Sulfonylureas and Imidazolinones Conferred by an Acetohydroxyacid Synthase Gene with Separate Mutations for Selective Resistance," Molecular Genetics, 1992, pp. 167-173, vol. 232.

Lee, Y., et al., "Effect of Mutagenesis at Serine 653 of *Arabidopsis thaliana* Acetohydroxyacid Synthase on the Sensitivity to Imidazolinone and Sulfonylurea Herbicides," FEBS Letters, 1999, pp. 341-345, vol. 452, Federation of European Biochemical Societies.

Mourad, G., et al., "Isolation and Genetic Analysis of a Triazolopyrimidine-Resistant Mutant of *Arabidopsis*," J Heredity, 1993, pp. 91-96, vol. 84.

Newhouse, K., et al., "Mutations in corn (*Zea mays* L.) Conferring Resistance to Imidazolinone Herbicides," Theor. Appl. Genet., 1991, pp. 65-70, vol. 83, Springer-Verlag.

Newhouse, K., et al., "Tolerance to Imidazolinone Herbicides in Wheat," Plant Physiology, 1992, pp. 882-886, vol. 100.

Odell, et al., "Comparison of Increased Expression of Wild-Type and Herbicide Resistant Acetolactate Synthase Genes in Transgenic Plants, and Indication of Posttranscriptional Limitation on Enzyme Activity," Plant Physiol., (1990), pp. 1647-1654, vol. 94.

Ott, K., et al., "Rational Molecular Design and Genetic Engineering of Herbicide Resistant Crops by Structure Modeling and Site-directed Mutagenesis of Acetohydroxyacid Synthase," J Mol. Biol., 1996, pp. 359-368, vol. 263, Academic Press Limited.

Repellin, A., et al., "Genetic Enrichment of Cereal Crops via Alien Gene Transfer: New Challenges," Plant Cell, Tissue and Organ Culture, 2001, pp. 159-183, vol. 64.

Sathasivan, K., et al., "Nucleotide Sequence of a Mutant Acetolactate synthase Gene from an Imidaziolinone-resistant *Arabidopsis thaliana* var. Columbia," Nucleic Acids Research, 1990, pp. 2188, vol. 18(8), Oxford University Press.

Sathasivan, K., et al., "Molecular Basis of Imidazolinone Herbicide Resistance in *Arabidopsis thaliana* var Columbia," Plant Physiol., 1991, pp. 1044-1050, vol. 97.

Paul R. Schmitzer et al., "Lack of Cross-Resistance of Imazaquin-Resistant Xanthiu strumarium Acetolactate Synthase to Flumetsulam and Chlorimuron", Plant Physiol., vol. 103, 1993, pp. 281-283.

Sebastian, S., et al., "Semidominant Soybean Mutation for Resistance to Sulfonylurea Herbicides," Crop. Sci., 1989, pp. 1403-1408, vol. 29.

Shaner, D., et al., "Imidazolinone-Resistant Crops: Selection, Characterization, and Management," Herbicide-Resistant Crops: Agricultural, Environmental, Economic, 1996, pp. 143-157.

Shaner, D. and P.A. Robson, "Absorption, Translocation, and Metabolism of AC 25 214 in Soybean (*Glycine max*), Common Cocklebur (*Xanthium strumarium*), and Velvetlea (*Abutilon theophrasti*)," Weed Sci., 1985, pp. 469-471, vol. 33.

Shaner, D., et al., "Imidazolinones: Potent Inhibitors of Acetohydroxyacid Synthase," Plant Physiol., 1984, pp. 545-546, vol. 76.

Singh, B.K., "Biosynthesis of Valine, Leucine and Isoleucine," Plant Amino Acids, 1999, pp. 227-247, Marcel Dekker Inc., New York, NY.

Seefeldt, S., et al., "Production of Herbicide-Resistant Jointed Goatgrass (*Aegilops cylindrical*) x Wheat (*Triticum aestivum*) Hybrids in the Field by Natural Hybridization," Weed Science, 1998, pp. 632-634, vol. 46.

Swanson, E., et al., "Microspore Mutagenesis and Selection: Canola Plants with Field Tolerance to the Imidazolinones," Theor. Appl. Genet., 1989, pp. 525-530, vol. 78, Springer-Verlag.

White, A., et al., "Common sunflower resistance to acetolactate synthase-inhibiting herbicides," Weed Science, 2002, pp. 432-437, vol. 50.

Wright, T.R. and D. Penner, "Cell Selection and Inheritance of Imidazolinone Resistance in Sugarbeet (*Beta vulgaris*)," Theor. Appl. Genet., 1998, pp. 612-620, vol. 96, Springer-Verlag.

Zhu, T. et al., "Engineering herbicide-resistant maize using chimeric RNA/DNA oligonucleotides", Nature Biotechnology, 2000, pp. 555-558, vol. 18.

GenBank Accession No. BE417248. Created Jul. 24, 2000.
GenBank Accession No. BF200418. Created Nov. 6, 2000.
EMBL Accession No. AF059600. Created Apr. 27, 1998.
Lee, et al., "Single nucleotide mutation in the barley acetohydroxy acid synthase (AHAS) gene confers resistance to midazolinone herbicides", Proc Natl Acad Sci USA. May 2, 20114;108 (21):8909-13, United States National Academy of Sciences, United States.

* cited by examiner

Figure 2A

Inhibition of AHAS Enzyme Activity in wild-type wheat (variety Gunner) and AP205CL

| Imazamox Conc. (µM) | Gunner Wild-type | AP205CL |
|---|---|---|
| 100.0 | 4 | 28 |
| 50.0 | 7 | 36 |
| 25.0 | 8 | 37 |
| 13.0 | 12 | 41 |
| 6.0 | 19 | 47 |
| 3.0 | 34 | 58 |
| 2.0 | 53 | 70 |
| 1.0 | 77 | 87 |

Figure 2B

Inhibition of AHAS Enzyme Activity in wild-type wheat (variety Gunner) and AP602CL

| Imazamox Conc. (µM) | Gunner Wild-type | AP602CL |
|---|---|---|
| 100.0 | 15.1 | 43.5 |
| 50.0 | 16.5 | 46.3 |
| 25.0 | 25.4 | 49.6 |
| 12.5 | 43.4 | 53.7 |
| 6.3 | 59.6 | 61.9 |
| 3.1 | 83.6 | 71.8 |
| 1.6 | 99.8 | 84.3 |

Figure 2C

Inhibition of AHAS Enzyme Activity in wild-type wheat (variety Madsen) and Madsen1

| µM IMI Herbicide | % Uninhibited AHAS Activity | |
|---|---|---|
|  | Madsen WT | Madsen1 |
| 100.0 | 0.0 | 22.2 |
| 50.0 | 1.7 | 24.5 |
| 25.0 | 2.7 | 25.3 |
| 12.5 | 6.0 | 27.7 |
| 6.3 | 12.0 | 34.8 |
| 3.1 | 25.4 | 42.0 |
| 1.6 | 42.3 | 53.6 |
| 0.8 | 64.2 | 72.2 |

Figure 3

Decreased Injury of Madsen1 by Imazamox as Compared to Teal wheat control

| Wheat Cultivar | Injury Score | |
|---|---|---|
| | 40 g/ha Imazamox | 80 g/ha Imazamox |
| Madsen1 | 3.3 | 5.1 |
| Teal Control | 8.9 | 9.0 |

Figure 4A

Feedback Inhibition of AHAS Enzyme Activity by Leucine and Valine in wild-type wheat (variety Gunner) and AP205CL

| Leucine & Valine Conc. (μM) | Gunner Wild-type | AP205CL |
|---|---|---|
| 1000.0 | 42 | 44 |
| 500.0 | 48 | 48 |
| 250.0 | 56 | 50 |
| 125.0 | 65 | 58 |
| 63.0 | 75 | 70 |
| 31.3 | 83 | 82 |
| 15.6 | 92 | 90 |
| 7.8 | 98 | 95 |

Figure 4B

Feedback Inhibition of AHAS Enzyme Activity by Leucine and Valine in wild-type wheat (variety Gunner) and AP602CL

| Leucine & Valine Conc. (μM) | Gunner Wild-type | AP602CL |
|---|---|---|
| 1000.0 | 46.9 | 48.7 |
| 500.0 | 53.6 | 49.4 |
| 250.0 | 65.9 | 56.7 |
| 125.0 | 74.5 | 68.2 |
| 63.0 | 82.4 | 79.5 |
| 31.3 | 89.3 | 86.6 |
| 15.6 | 98.6 | 93.1 |
| 7.8 | 102.8 | 98.7 |

WHEAT PLANTS HAVING INCREASED RESISTANCE TO IMIDAZOLINONE HERBICIDES

CROSS-REFERENCE TO RELATED APPLICATIONS

This application is a continuation of U.S. patent application Ser. No. 15/290,128, filed Oct. 11, 2016, which is a continuation of U.S. patent application Ser. No. 13/784,037, filed Mar. 4, 2013, which is a divisional of U.S. patent application Ser. No. 12/362,935, filed Jan. 30, 2009, now U.S. Pat. No. 8,389,809, issued on Mar. 5, 2013, which is a divisional of U.S. patent application Ser. No. 10/486,595, filed Sep. 13, 2004, now U.S. Pat. No. 7,528,397, issued on May 5, 2009, which is the U.S. National Stage of International Application PCT/US02/21753, filed Jul. 10, 2002, which published in English on Feb. 20, 2003 and designates the U.S., which claims the priority benefit of U.S. Provisional Application Ser. No. 60/311,141 filed Aug. 9, 2001; all of which are hereby incorporated herein in their entirety by reference.

FIELD OF THE INVENTION

The present invention relates in general to plants having an increased resistance to imidazolinone herbicides. More specifically, the present invention relates to wheat plants obtained by mutagenesis and cross-breeding and transformation that have an increased resistance to imidazolinone herbicides.

BACKGROUND OF THE INVENTION

Acetohydroxyacid synthase (AHAS; EC 4.1.3.18) is the first enzyme that catalyzes the biochemical synthesis of the branched chain amino acids valine, leucine and isoleucine (Singh B. K., 1999 Biosynthesis of valine, leucine and isoleucine in: Singh B. K. (Ed) Plant amino acids. Marcel Dekker Inc. New York, N.Y. Pg 227-247). AHAS is the site of action of four structurally diverse herbicide families including the sulfonylureas (LaRossa R A and Falco S C, 1984 Trends Biotechnol 2:158-161), the imidazolinones (Shaner et al., 1984 Plant Physiol 76:545-546), the triazolopyrimidines (Subramanian and Gerwick, 1989 Inhibition of acetolactate synthase by triazolopyrimidines in (ed) Whitaker J R, Sonnet P E Biocatalysis in agricultural biotechnology. ACS Symposium Series, American Chemical Society. Washington, D.C. Pg 277-288), and the pyrimidyloxybenzoates (Subramanian et al., 1990 Plant Physiol 94: 239-244). Imidazolinone and sulfonylurea herbicides are widely used in modern agriculture due to their effectiveness at very low application rates and relative non-toxicity in animals. By inhibiting AHAS activity, these families of herbicides prevent further growth and development of susceptible plants including many weed species. Several examples of commercially available imidazolinone herbicides are PURSUIT® (imazethapyr), SCEPTER® (imazaquin) and ARSENAL® (imazapyr). Examples of sulfonylurea herbicides are chlorsulfuron, metsulfuron methyl, sulfometuron methyl, chlorimuron ethyl, thifensulfuron methyl, tribenuron methyl, bensulfuron methyl, nicosulfuron, ethametsulfuron methyl, rimsulfuron, triflusulfuron methyl, triasulfuron, primisulfuron methyl, cinosulfuron, amidosulfuron, fluzasulfuron, imazosulfuron, pyrazosulfuron ethyl and halosulfuron.

Due to their high effectiveness and low-toxicity, imidazolinone herbicides are favored for application by spraying over the top of a wide area of vegetation. The ability to spray an herbicide over the top of a wide range of vegetation decreases the costs associated with plantation establishment and maintenance and decreases the need for site preparation prior to use of such chemicals. Spraying over the top of a desired tolerant species also results in the ability to achieve maximum yield potential of the desired species due to the absence of competitive species. However, the ability to use such spray-over techniques is dependent upon the presence of imidazolinone resistant species of the desired vegetation in the spray over area.

Among the major agricultural crops, some leguminous species such as soybean are naturally resistant to imidazolinone herbicides due to their ability to rapidly metabolize the herbicide compounds (Shaner and Robinson, 1985 Weed Sci. 33:469-471). Other crops such as corn (Newhouse et al., 1992 Plant Physiol. 100:882-886) and rice (Barrette et al., 1989 Crop Safeners for Herbicides, Academic Press New York, pp. 195-220) are somewhat susceptible to imidazolinone herbicides. The differential sensitivity to the imidazolinone herbicides is dependent on the chemical nature of the particular herbicide and differential metabolism of the compound from a toxic to a non-toxic form in each plant (Shaner et al., 1984 Plant Physiol. 76:545-546; Brown et al., 1987 Pestic. Biochm. Physiol. 27:24-29). Other plant physiological differences such as absorption and translocation also play an important role in sensitivity (Shaner and Robinson, 1985 Weed Sci. 33:469-471).

Crop cultivars resistant to imidazolinones, sulfonylureas and triazolopyrimidines have been successfully produced using seed, microspore, pollen, and callus mutagenesis in *Zea Mays, Arabidopsis thaliana, Brassica napus, Glycine max*, and *Nicotiana tabacum* (Sebastian et al., 1989 Crop Sci. 29:1403-1408; Swanson et al., 1989 Theor. Appl. Genet. 78:525-530; Newhouse et al., 1991 Theor. Appl. Genet 83:65-70; Sathasivan et al., 1991 Plant Physiol. 97:1044-1050; Mourand et al., 1993 J. Heredity 84:91-96). In all cases, a single, partially dominant nuclear gene conferred resistance. Four imidazolinone resistant wheat plants were also previously isolated following seed mutagenesis of *Triticum aestivum* L. cv Fidel (Newhouse et al., 1992 Plant Physiol. 100:882-886). Inheritance studies confirmed that a single, partially dominant gene conferred resistance. Based on allelic studies, the authors concluded that the mutations in the four identified lines were located at the same locus. One of the Fidel cultivar resistance genes was designated FS-4 (Newhouse et al., 1992 Plant Physiol. 100:882-886).

Computer-based modeling of the three dimensional conformation of the AHAS-inhibitor complex predicts several amino acids in the proposed inhibitor binding pocket as sites where induced mutations would likely confer selective resistance to imidazolinones (Ott et al., 1996 J. Mol. Biol. 263:359-368) Wheat plants produced with some of these rationally designed mutations in the proposed binding sites of the AHAS enzyme have in fact exhibited specific resistance to a single class of herbicides (Ott et al., 1996 J. Mol. Biol. 263:359-368).

Plant resistance to imidazolinone herbicides has also been reported in a number of patents. U.S. Pat. Nos. 4,761,373, 5,331,107, 5,304,732, 6,211,438, 6,211,439 and 6,222,100 generally describe the use of an altered AHAS gene to elicit herbicide resistance in plants, and specifically discloses certain imidazolinone resistant corn lines. U.S. Pat. No. 5,013,659 discloses plants exhibiting herbicide resistance possessing mutations in at least one amino acid in one or more conserved regions. The mutations described therein encode either cross-resistance for imidazolinones and sulfonylureas or sulfonylurea-specific resistance, but imidazolinone-specific resistance is not described. Additionally, U.S. Pat. Nos. 5,731,180 and 5,767,361 discuss an isolated gene having a single amino acid substitution in a wild-type monocot AHAS amino acid sequence that results in imidazolinone-specific resistance.

To date, the prior art has not described imidazolinone resistant wheat plants containing more than one altered AHAS gene. Nor has the prior art described imidazolinone resistant wheat plants containing mutations on genomes other than the genome from which the FS-4 gene is derived. Therefore, what is needed in the art is the identification of imidazolinone resistance genes from additional genomes. What are also needed in the art are wheat plants having increased resistance to herbicides such as imidazolinone and containing more than one altered AHAS gene. Also needed are methods for controlling weed growth in the vicinity of such wheat plants. These compositions and methods would allow for the use of spray over techniques when applying herbicides to areas containing wheat plants.

SUMMARY OF THE INVENTION

The present invention provides wheat plants comprising IMI nucleic acids, wherein the wheat plant has increased resistance to an imidazolinone herbicide as compared to a wild-type variety of the plant. The wheat plants can contain one, two, three or more IMI nucleic acids. In one embodiment, the wheat plant comprises multiple IMI nucleic acids located on different genomes. Preferably, the IMI nucleic acids encode proteins comprising a mutation in a conserved amino acid sequence selected from the group consisting of a Domain A, a Domain B, a Domain C, a Domain D and a Domain E. More preferably, the mutation is in a conserved Domain E or a conserved Domain C. Also provided are plant parts and plant seeds derived from the wheat plants described herein. In another embodiment, the wheat plant comprises an IMI nucleic acid that is not an Imi1 nucleic acid. The IMI nucleic acid can be an Imi2 or Imi3 nucleic acid, for example.

The IMI nucleic acids of the present invention can comprise a nucleotide sequence selected from the group consisting of: a polynucleotide of SEQ ID NO:1; a polynucleotide of SEQ ID NO:3; a polynucleotide of SEQ ID NO:5; a polynucleotide comprising at least 60 consecutive nucleotides of any of the aforementioned polynucleotides; and a polynucleotide complementary to any of the aforementioned polynucleotides.

The plants of the present invention can be transgenic or non-transgenic. Examples of non-transgenic wheat plants having increased resistance to imidazolinone herbicides include a wheat plant having an ATCC Patent Deposit Designation Number PTA-4213, PTA-4214 or PTA-4255; or a mutant, recombinant, or genetically engineered derivative of the plant with ATCC Patent Deposit Designation Number PTA-4213, PTA-4214 or PTA-4255; or of any progeny of the plant with ATCC Patent Deposit Designation Number PTA-4213, PTA-4214 or PTA-4255; or a plant that is a progeny of any of these plants.

In addition to the compositions of the present invention, several methods are provided. Described herein are methods of modifying a plant's tolerance to an imidazolinone herbicide comprising modifying the expression of an IMI nucleic acid in the plant. Also described are methods of producing a transgenic plant having increased tolerance to an imidazolinone herbicide comprising, transforming a plant cell with an expression vector comprising one or more IMI nucleic acids and generating the plant from the plant cell. The invention further includes a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant and wherein the plant comprises one or more IMI nucleic acids. In some preferred embodiments of these methods, the plants comprise multiple IMI nucleic acids that are located on different wheat genomes.

BRIEF DESCRIPTION OF THE DRAWINGS

FIGS. 2A-C are tables showing the inhibition of AHAS enzyme activity in wild-type wheat (variety Gunner), AP205CL (FIG. 2A), AP602CL (FIG. 2B) and Madsen1 (FIG. 2C) by imidazolinone herbicide imazamox. Values are expressed as a percent of uninhibited activity.

FIG. 3 is a table showing the decreased injury of Madsen1 by imazamox as compared to a Teal wheat control.

FIGS. 4A-B are tables showing the feedback inhibition of AHAS enzyme activity by leucine and valine in wild-type wheat (variety Gunner), AP205CL (FIG. 4A) and AP602CL (FIG. 4B).

DETAILED DESCRIPTION

Figure 1:
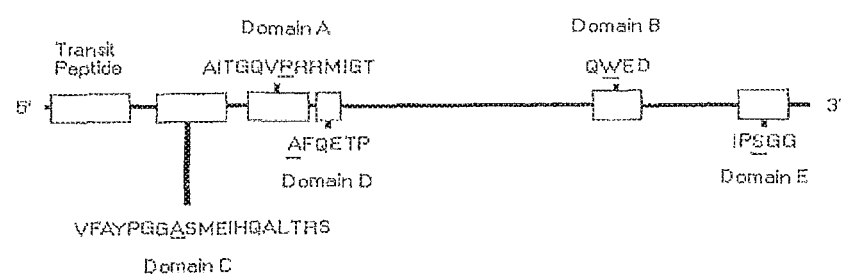
FIG. 1 is a schematic representation of the conserved amino acid sequences in the AHAS genes implicated in resistance to various AHAS inhibitors. The specific amino acid site responsible for resistance is indicated by an underline. (Modified from Devine, M. D. and Eberlein, C. V., 1997 Physiological, biochemical and molecular aspects of herbicide resistance based on altered target sites in Herbicide Activity: Toxicity, Biochemistry, and Molecular Biology, IOS Press Amersterdam, p. 159-185).

The present invention is directed to wheat plants, wheat plant parts and wheat plant cells having increased resistance to imidazolinone herbicides. The present invention also includes seeds produced by the wheat plants described herein and methods for controlling weeds in the vicinity of the wheat plants described herein. It is to be understood that as used in the specification and in the claims, "a" or "an" can mean one or more, depending upon the context in which it is used. Thus, for example, reference to "a cell" can mean that at least one cell can be utilized.

As used herein, the term "wheat plant" refers to a plant that is a member of the *Triticum* genus. The wheat plants of the present invention can be members of a *Triticum* genus including, but not limited to, *T. aestivum, T. turgidum, T timopheevii, T. monococcum, T. zhukovskyi* and *T. urartu* and hybrids thereof. Examples of *T aestivum* subspecies included within the present invention are *aestivum* (common wheat), *compactum* (club wheat), *macha* (*macha* wheat), *vavilovi* (*vavilovi* wheat), *spelta* and *sphaecrococcum* (shot wheat). Examples of *T. turgidum* subspecies included within the present invention are *turgidum, carthlicum, dicoccon, durum, paleocolchicum, polonicum, turanicum* and *dicoccoides*. Examples of *T. monococcum* subspecies included within the present invention are *monococcum* (einkorn) and *aegilopoides*. In one embodiment of the present invention, the wheat plant is a member of the *Triticum aestivum* L. species, and more particularly, a Gunner or Madsen cultivar.

The term "wheat plant" is intended to encompass wheat plants at any stage of maturity or development as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts and the like. The present invention also includes seeds produced by the wheat plants of the present invention. In one embodiment, the seeds are true, breeding for an increased resistance to an imidazolinone herbicide as compared to a wild type variety of the wheat plant seed.

The present invention describes a wheat plant comprising one or more IMI nucleic acids, wherein the wheat plant has increased resistance to an imidazolinone herbicide as compared to a wild-type variety of the plant. As used herein, the term "IMI nucleic acid" refers to a nucleic acid that is mutated from an AHAS nucleic acid in a wild type wheat plant that confers increased imidazolinone resistance to a plant in which it is transcribed. In one embodiment, the wheat plant comprises multiple IMI nucleic acids. As used when describing the IMI nucleic acids, the term "multiple" refers to IMI nucleic acids that have different nucleotide sequences and does not refer to a mere increase in number of the same IMI nucleic acid. For example, the IMI nucleic acids can be different due to the fact that they are derived from or located on different wheat genomes.

It is possible for the wheat plants of the present invention to have multiple IMI nucleic acids from different genomes since these plants can contain more than one genome. For example, a *Triticum aestivum* wheat plant contains three genomes sometimes referred to as the A, B and D genomes. Because AHAS is a required metabolic enzyme, it is assumed that each genome has at least one gene coding for the AHAS enzyme, commonly seen with other metabolic enzymes in hexaploid wheat that have been mapped. The AHAS nucleic acid on each genome can, and usually does, differ in its nucleotide sequence from an AHAS nucleic acid on another genome. One of skill in the art can determine the genome of origin of each AHAS nucleic acid through genetic crossing and/or either, sequencing methods or exonuclease digestion methods known to those of skill in the art and as also described in Example 2 below. For the purposes of this invention, IMI nucleic acids derived from one of the A, B or D genomes are distinguished and designated as Imi1, Imi2 or Imi3 nucleic acids. It is not stated herein that any particular Imi nucleic acid class correlates with any particular A, B or D genome. For example, it is not stated herein that the Imi1 nucleic acids correlate to A genome nucleic acids, that Imi2 nucleic acids correlate to B genome nucleic acids, etc. The Imi1, Imi2 and Imi3 designations merely indicate that the IMI nucleic acids within each such class do not segregate independently, whereas two IMI nucleic acids from different classes do segregate independently and may therefore be derived from different wheat genomes.

The Imi1 class of nucleic acids includes the FS-4 gene as described by Newhouse et al. (1992 Plant Physiol. 100:882-886) and the Gunner IMI1 205 gene described in more detail below. The Imi2 class of nucleic acids includes the Gunner IMI2 208 gene and the Madsen IMI2 gene described below. As shown from the members of the Imi1 class of nucleic acids, each Imi class can include members from different wheat species. Therefore, each Imi class includes IMI nucleic acids that differ in their nucleotide sequence but that are nevertheless designated as originating from, or being located on, the same wheat genome using inheritance studies as known to those of ordinary skill in the art.

Accordingly, the present invention includes a wheat plant comprising one or more IMI nucleic acids, wherein the wheat plant has increased resistance to an imidazolinone herbicide as compared to a wild-type variety of the plant and wherein the one or more IMI nucleic acids are selected from a group consisting of an Imi1, Imi2 and Imi3 nucleic acid. In one embodiment, the plant comprises an Imi1 nucleic and an Imi2 nucleic acid. In a preferred embodiment, the Imi1 nucleic acid comprises the polynucleotide sequence shown in SEQ ID NO:1 and the Imi2 nucleic acid comprises the polynucleotide sequence shown in SEQ ID NO:3 or SEQ ID NO:5. In another embodiment, the plant comprises an Imi3 nucleic acid.

As used herein with regard to nucleic acids, the term "from" refers to a nucleic acid "located on" or "derived from" a particular genome. The term "located on refers to a nucleic acid contained within that particular genome. As also used herein with regard to a genome, the term "derived from" refers to a nucleic acid that has been removed or isolated from that genome. The term "isolated" is defined in more detail below.

In another embodiment, the wheat plant comprises an IMI nucleic acid, wherein the nucleic acid is a non-Imi1 nucleic acid. The term "non-Imi1", refers to an IMI nucleic acid that is not a member of the Imi1 class as described above. Examples of non-Imi1 nucleic acid are the polynucleotide sequences shown in SEQ ID NO:3 and SEQ. NO:5. Accordingly, in a preferred embodiment, the wheat plant comprises an IMI nucleic acid comprising the polynucleotide sequence shown in SEQ ID NO:3 or SEQ ID NO:5.

The present invention includes wheat plants comprising one, two, three or more IMI nucleic acids, wherein the wheat plant has increased resistance to an imidazolinone herbicide as compared to a wild-type variety of the plant. The IMI nucleic acids can comprise a nucleotide sequence selected from the group consisting of a polynucleotide of SEQ ID NO:1; a polynucleotide of SEQ ID NO:3; a polynucleotide of SEQ ID NO:5; a polynucleotide encoding a polypeptide of SEQ ID NO:2, a polynucleotide encoding a polypeptide of SEQ ID NO:4; a polynucleotide encoding a polypeptide of SEQ ID NO:6; a polynucleotide comprising at least 60 consecutive nucleotides of any of the aforementioned polynucleotides; and a polynucleotide complementary to any of the aforementioned polynucleotides.

The imidazolinone herbicide can be selected from, but is not limited to, PURSUIT® (imazethapyr), CADRE® (imazapic), RAPTOR® (imazamox), SCEPTER® (imazaquin), ASSERT® (imazethabenz), ARSENAL® (imazapyr), a derivative of any of the aforementioned herbicides, or a mixture of two or more of the aforementioned herbicides, for example, imazapyr/imazamox (ODYSSEY®). More specifically, the imidazolinone herbicide can be selected from, but is not limited to, 2-(4-isopropyl-4-methyl-5-oxo-2-imidazolin-2-yl)-nicotinic acid, 2-(4-isopropyl-4-methyl-5-oxo-2-imidazolin-2-yl)-3-quinolinecarboxylic acid, 5-ethyl-2-(4-isopropyl-4-methyl-5-oxo-2-imidazolin-2-yl)-nicotinic acid, 2-(4-isopropyl-4-methyl-5-oxo-2-imidazolin-2-yl)-5-(methoxymethyl)-nicotinic acid, 2-(4-isopropyl-4-methyl-5-oxo-2-imidazolin-2-yl)-5-methylnicotinic acid, and a mixture of methyl 6-(4-isopropyl-4-methyl-5-oxo-2-imidazolin-2-yl)-m-toluate and methyl 2-(4-isopropyl-4-methyl-5-oxo-2-imidazolin-2-yl)-p-toluate. The use of 5-ethyl-2-(4-isopropyl-4-methyl-5-oxo-2-imidazolin-2-yl)-nicotinic acid and 2-(4-isopropyl-4-methyl-5-oxo-2-imidazolin-2-yl)-5-(methoxymethyl)-nicotinic acid is preferred. The use of 2-(4-isopropyl-4-methyl-5-oxo-2-imidazolin-2-yl)-5-(methoxymethyl)-nicotinic acid is particularly preferred.

In one embodiment, the wheat plant comprises two IMI nucleic acids, wherein the nucleic acids are derived from or located on different wheat genomes. Preferably, the two nucleic acids are an Imi1 nucleic acid and an Imi2 nucleic acid. More preferably, the Imi1 nucleic acid comprises the polynucleotide sequence of SEQ ID NO:1 and the Imi2 nucleic acid comprises the polynucleotide sequence of SEQ ID NO:3 or SEQ ID NO:5. In another embodiment, the wheat plant comprises one IMI nucleic acid, wherein the nucleic acid comprises the polynucleotide sequence of SEQ ID NO:1, SEQ ID NO:3 or SEQ ID NO:5. In yet another embodiment, the wheat plant comprises three or more IMI nucleic acids wherein each nucleic acid is from a different genome. Preferably, at least one of the three IMI nucleic acids comprises a polynucleotide sequence selected from the group consisting of SEQ ID NO:1, SEQ ID NO:3 and SEQ ID NO:5.

In a preferred embodiment of the present invention, the one or more IMI nucleic acids contained within the plant encode an amino acid sequence comprising a mutation in a domain that is conserved among several AHAS proteins. These conserved domains are referred to herein as Domain A, Domain B, Domain C, Domain D and Domain E. FIG. 1 shows the general location of each domain in an AHAS protein. Domain A contains the amino acid sequence AITGQVPRRMIGT (SEQ ID NO:7). Domain B contains the amino acid sequence QWED (SEQ ID NO:8). Domain C contains the amino acid sequence VFAYPGGAS-MEIHQALTRS (SEQ ID NO:9). Domain D contains the amino acid sequence AFQETP (SEQ ID NO:10). Domain E contains the amino acid sequence IPSGG (SEQ ID NO:11). The present invention also contemplates that there may be slight variations in the conserved domains, for example; in cockleberry plants, the serine residue in Domain E is replaced by an alanine residue.

Accordingly, the present invention includes a wheat plant comprising an IMI nucleic acid that encodes an amino acid sequence having a mutation in a conserved domain selected from the group consisting of a Domain A, a Domain B, a Domain C, a Domain D and a Domain E. In one embodiment, the wheat plant comprises an IMI nucleic acid that encodes an amino acid sequence having a mutation in a Domain E. In further preferred embodiments, the mutations in the conserved domains occur at the locations indicated by the following underlining: AITGQVPRRMIGT (SEQ ID NO:7); QWED (SEQ ID NO:8); VFAYPGGASMEIHQAL-TRS (SEQ ID NO:9); AFQETP (SEQ ID NO:10) and IPSGG (SEQ ID NO:11). One preferred substitution is asparagine for serine in Domain E (SEQ ID NO:11).

The wheat plants described herein can be either transgenic wheat plants or non-transgenic wheat plants. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding. Plants containing mutations arising due to non-spontaneous mutagenesis and selective breeding are referred to herein as non-transgenic plants and are included in the present invention. In embodiments wherein the wheat plant is transgenic and comprises multiple IMI nucleic acids, the nucleic acids can be derived from different genomes or from the same genome. Alternatively, in embodiments wherein the wheat plant is non-transgenic and comprises multiple IMI nucleic acids, the nucleic acids are located on different genomes or on the same genome.

An example of a non-transgenic wheat plant cultivar comprising one IMI nucleic acid is the plant cultivar deposited with the ATCC under Patent Deposit Designation Number Accession PTA-4213 as hard red spring bread wheat, *Triticum aestivum*, G205, the deposit having been made on Apr. 9, 2002 with the American Type Culture Collection (ATCC) located at 10801 University Blvd, Manassess, Va. 20110-2209, an International Depository Authority (IDA) under the Budapest Treaty, and designated herein as the Gunner IMI 205 wheat cultivar. The wheat plant cultivar PTA-4213 was deposited and accepted under the terms of the Budapest Treaty. The Gunner IMI 205 wheat cultivar contains an Imi1 nucleic acid. The partial nucleotide sequences corresponding to the Gunner IMI1 205 gene is shown in SEQ ID NO:1.

Another example of a non-transgenic wheat plant cultivar comprising one IMI nucleic acid is the plant cultivar deposited with the ATCC under Patent Deposit Designation Accession Number PTA-4214 as hard red spring bread wheat, *Triticum aestivum*, G208, the deposit having been made on Apr. 9, 2002 with the American Type Culture Collection (ATCC) located at 10801 University Blvd, Manassess, Va. 20110-2209, an International Depository Authority (IDA) under the Budapest Treaty, and designated herein as the Gunner IMI 208 wheat cultivar. The wheat plant cultivar PTA-4214 was deposited and accepted under the terms of the Budapest Treaty. The Gunner IMI 208 wheat cultivar contains an Imi2 nucleic acid. The partial nucleotide sequence corresponding to the Gunner IMI2 208 gene is shown in SEQ ID NO:3.

Yet another example of a non-transgenic wheat plant cultivar comprising one IMI nucleic acid is the plant cultivar deposited with the ATCC under Patent Deposit Designation Accession Number PTA-4255 as *Triticum aestivum*, MAD1, the deposit having been made on May 28, 2002 with the American Type Culture Collection (ATCC) located at 10801 University Blvd, Manassess, Va. 20110-2209, an International Depository Authority (IDA) under the Budapest Treaty, and designated herein as the Madsen IMI wheat cultivar. The wheat plant cultivar PTA-4255 was deposited and accepted under the terms of the Budapest Treaty. The Madsen IMI wheat cultivar contains an Imi2 nucleic acid. The partial nucleotide sequence corresponding to the Madsen IMI2 gene is shown in SEQ ID NO:5.

Separate deposits of 2500 seeds of the Gunner IMI 205, Gunner IMI 208 and Madsen IMI wheat cultivars were made with the American Type Culture Collection, Manassas, Va. on Apr. 9, 2002 (Gunner IMI 205 and Gunner IMI 208) and on May 1, 2002 (Madsen IMI). These deposits were made in accordance with the terms and provisions of the Budapest Treaty relating to the deposit of microorganisms. The deposits were made for a term of at least thirty years and at least five years after the most recent request for the furnishing of a sample of the deposit is received by the ATCC. The deposited seeds were accorded Patent Deposit Designation Numbers PTA-4213 (Gunner IMI 205), PTA-4214 (Gunner IMI 208) and PTA-4255 (Madsen IMI).

The present invention includes the wheat plant having a Patent Deposit Designation Number PTA-4213, PTA-4214 or PTA-4255; a mutant, recombinant, or genetically engineered derivative of the plant with Patent Deposit Designation Number PTA-4213, PTA-4214 or PTA-4255; any progeny of the plant with Patent Deposit Designation Number PTA-4213, PTA-4214 or PTA-4255; and a plant that is the progeny of any of these plants. In a preferred embodiment, the wheat plant of the present invention additionally has the herbicide resistance characteristics of the plant with Patent Deposit Designation Number PTA-4213, PTA-4214 or PTA-4255.

Also included in the present invention are hybrids of the Gunner IMI 205, Gunner IMI 208 or Madsen IMI wheat cultivars described herein and another wheat cultivar. The other wheat cultivar includes, but is not limited to, *T. aestivum* L. cv Fidel and any wheat cultivar harboring a mutant gene FS-1, FS-2, FS-3 or FS-4. (See U.S. Pat. No. 6,339,184 and U.S. patent application Ser. No. 08/474,832). Preferred hybrids contain a combination of Imi1, Imi2 and/or Imi3 nucleic acids. Examples of preferred hybrids are Gunner IMI 205/Gunner IMI 208 hybrids. The Gunner IMI 205/Gunner IMI 208 hybrids comprise an Imi1 nucleic acid and an Imi2 nucleic acid.

The terms "cultivar" and "variety" refer to a group of plants within a species defined by the sharing of a common set of characteristics or traits accepted by those skilled in the art as sufficient to distinguish one cultivar or variety from another cultivar or variety. There is no implication in either term that all plants of any given cultivar or variety will be genetically identical at either the whole gene or molecular level or that any given plant will be homozygous at all loci. A cultivar or variety is considered "true breeding" for a particular trait if, when the true-breeding cultivar or variety is self-pollinated, all of the progeny contain the trait. In the present invention, the trait arises from a mutation in an AHAS gene of the wheat plant or seed.

It is to be understood that the wheat plant of the present invention can comprise a wild type or non-mutated AHAS gene in addition to an IMI gene. As described in Examples 1 and 2, it is contemplated that the Gunner IMI 205, Gunner IMI 208 and Madsen IMI wheat cultivars contain a mutation in only one of multiple AHAS isoenzymes. Therefore, the present invention includes a wheat plant comprising one or more IMI nucleic acids in addition to one or more wild type or non-mutated AHAS nucleic acids.

In an embodiment, the present invention includes a wheat plant comprising multiple *Triticum* Imi nucleic acids, wherein the multiple Imi nucleic acids are from different genomes. A first of the multiple Imi nucleic acids is a B-genome Imi2 nucleic acid which, as a result of random mutagenesis, encodes an IMI2 polypeptide having a serine to asparagine substitution in Domain E as compared to a wild-type AHAS polypeptide. The multiple Imi nucleic acids confer increased tolerance to an AHAS inhibitor herbicide relative to that of a wild-type variety of the plant. The Imi2 nucleic acid encodes the IMI2 polypeptide of one of: (a) a plant of line Madsen M1, a representative sample of seed of the line having been deposited with ATCC under Patent Deposit Designation Number PTA-4255, wherein the IMI2 polypeptide of the plant of the line Madsen M1 comprises the serine to asparagine substitution in Domain E; or (b) a plant of line Gunner 208, a representative sample of seed of the line having been deposited with ATCC under Patent Deposit Designation Number PTA-4214, wherein the plant of the line Gunner 208 comprises the serine to asparagine substitution in Domain E.

In addition to wheat plants, the present invention encompasses isolated IMI proteins and nucleic acids. The nucleic acids comprise a polynucleotide selected from the group consisting of a polynucleotide of SEQ ID NO:1; a polynucleotide of SEQ ID NO:3; a polynucleotide of SEQ ID NO:5; a polynucleotide encoding a polypeptide of SEQ ID NO:2; a polynucleotide encoding a polypeptide of SEQ ID NO:4; a polynucleotide encoding a polypeptide of SEQ ID NO:6; a polynucleotide comprising at least 60 consecutive nucleotides of any of the aforementioned polynucleotides; and a polynucleotide complementary to any of the aforementioned polynucleotides. In a preferred embodiment, the IMI nucleic acid comprises a polynucleotide sequence of SEQ ID NO:1, SEQ ID NO:3 or SEQ ID NO:5.

The term "AHAS protein" refers to an acetohydroxyacid synthase protein and the term "IMI protein" refers to any AHAS protein that is mutated from a wild type AHAS protein and that confers increased imidazolinone resistance to a plant, plant cell, plant part, plant seed or plant tissue when it is expressed therein. In a preferred embodiment, the IMI protein comprises a polypeptide encoded by a polynucleotide sequence comprising SEQ ID NO:1, SEQ ID NO:3 or SEQ ID. NO:5. As also used herein, the terms "nucleic acid" and "polynucleotide" refer to RNA or DNA that is linear or branched, single or double stranded, or a hybrid thereof. The term also encompasses RNA/DNA hybrids. These terms also encompass untranslated sequence located at both the 3' and 5' ends of the coding region of the gene: at least about 1000 nucleotides of sequence upstream from the 5' end of the coding region and at least about 200 nucleotides of sequence downstream from the 3' end of the coding region of the gene. Less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made. The antisense polynucleotides and ribozymes can consist entirely of ribonucleotides, or can contain mixed ribonucleotides and deoxyribonucleotides. The polynucleotides of the invention may be produced by any means, including genomic preparations, cDNA preparations, in vitro synthesis, RT-PCR and in vitro or in vivo transcription.

An "isolated" nucleic acid molecule is one that is substantially separated from other nucleic acid molecules, which are present in the natural source of the nucleic acid (i.e., sequences encoding other polypeptides).

Preferably, an "isolated" nucleic acid is free of some of the sequences that naturally flank the nucleic acid (i.e., sequences located at the 5' and 3' ends of the nucleic acid) in its naturally occurring replicon. For example, a cloned nucleic acid is considered isolated. In various embodiments, the isolated IMI nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a *Triticum aestivum* cell). A nucleic acid is also considered isolated if it has been altered by human intervention, or placed in a locus or location that is not its natural site, or if it is introduced into a cell by agroinfection or biolistics. Moreover, an "isolated" nucleic acid molecule, such as a cDNA molecule, can be free from some of the other cellular material with which it is naturally associated, or culture medium when produced by recombinant techniques, or chemical precursors or other chemicals when chemically synthesized.

Specifically excluded from the definition of "isolated nucleic acids" are: naturally-occurring chromosomes (such as chromosome spreads), artificial chromosome libraries, genomic libraries, and cDNA libraries that exist either as an in vitro nucleic acid preparation or as a transfected/transformed host cell preparation, wherein the host cells are either an in vitro heterogeneous preparation or plated as a heterogeneous population of single colonies. Also, specifically excluded are the above libraries wherein a specified nucleic acid makes up less than 5% of the number of nucleic acid inserts in the vector molecules. Further specifically excluded are whole cell genomic DNA or whole cell RNA preparations (including whole cell preparations that are mechanically sheared or enzymatically digested). Even further specifically excluded are the whole cell preparations found as either an in vitro preparation or as a heterogeneous mixture separated by electrophoresis wherein the nucleic acid of the invention has not further been separated from the heterologous nucleic acids in the electrophoresis medium (e.g., further separating by excising a single band from a heterogeneous band population in an agarose gel or nylon blot).

A nucleic acid molecule of the present invention, e.g., a nucleic acid molecule containing a nucleotide sequence of SEQ ID NO:1, SEQ ID NO:3, SEQ ID NO:5 or a portion thereof, can be isolated using standard molecular biology techniques and the sequence information provided herein. For example, a *T. aestivum* IMI cDNA can be isolated from a *T aestivum* library using all or a portion of the sequence of SEQ ID NO:1, SEQ ID NO:3 or SEQ ID. NO:5. Moreover, a nucleic acid molecule encompassing all or a portion of SEQ ID NO:1, SEQ ID NO:3 or SEQ ID NO:5 can be isolated by the polymerase chain reaction using oligonucleotide primers designed based upon this sequence. For example, mRNA can be isolated from plant cells (e.g., by the guanidinium-thiocyanate extraction procedure of Chirgwin et al., 1979 Biochemistry 18:5294-5299) and cDNA can be prepared using reverse transcriptase (e.g., Moloney MLV reverse transcriptase, available from Gibco/BRL, Bethesda, Md.; or AMV reverse' transcriptase, available from Seikagaku America, Inc., St. Petersburg, Fla.). Synthetic oligonucleotide primers for polymerase chain reaction amplification can be designed based upon the nucleotide sequence shown in SEQ ID NO:1, SEQ ID NO:3 or SEQ ID NO:5. A nucleic acid molecule of the invention can be amplified using cDNA or, alternatively, genomic DNA, as a template and appropriate oligonucleotide primers according to standard PCR amplification techniques. The nucleic acid molecule so amplified can be cloned into an appropriate vector and characterized by DNA sequence analysis. Furthermore, oligonucleotides corresponding to an IMI nucleotide sequence can be prepared by standard synthetic techniques, e.g., using an automated DNA synthesizer.

The IMI nucleic acids of the present invention can comprise sequences encoding an IMI protein (i.e., "coding regions"), as well as 5' untranslated sequences and 3' untranslated sequences. Alternatively, the nucleic acid molecules of the present invention can comprise only the coding regions of an IMI gene, or can contain whole genomic fragments isolated from genomic DNA. A coding region of these sequences is indicated as an "ORF position". Moreover, the nucleic acid molecule of the invention can comprise a portion of a coding region of an IMI gene, for example, a fragment that can be used as a probe or primer.

The nucleotide sequences determined from the cloning of the IMI genes from *T aestivum* allow for the generation of probes and primers designed for use in identifying and/or cloning IMI homologs in other cell types and organisms, as well as IMI homologs from other wheat plants and related species. The portion of the coding region can also encode a biologically active fragment of an IMI protein.

As used herein, the term "biologically active portion of an IMI protein is intended to include a portion, e.g., a domain/motif, of an IMI protein that, when produced in a plant increases the plant's resistance to an imidazolinone herbicide as compared to a wild-type variety of the plant. Methods for quantitating increased resistance to imidazolinone herbicides are provided in the Examples below. Biologically active portions of an IMI protein include peptides comprising SEQ ID NO:2, SEQ ID NO:4 or SEQ ID NO:6 which include fewer amino acids than a full length IMI protein and impart increased resistance to an imidazolinone herbicide upon expression in a plant. Typically, biologically active portions (e.g., peptides which are, for example, 5, 10, 15, 20, 30, 35, 36, 37, 38, 39, 40, 50, 100 or more amino acids in length) comprise a domain or motif with at least one activity of an IMI protein. Moreover, other biologically active portions in which other regions of the polypeptide are deleted, can be prepared by recombinant techniques and evaluated for one or more of the activities described herein. Preferably, the biologically active portions of an IMI protein include one or more conserved domains selected from the group consisting of a Domain A, a Domain B, a Domain C, a Domain D and a Domain E, wherein the conserved domain contains a mutation.

The invention also provides IMI chimeric or fusion polypeptides. As used herein, an IMI "chimeric polypeptide" or "fusion polypeptide" comprises an IMI polypeptide operably linked to a non-IMI polypeptide. A "non-IMI polypeptide" refers to a polypeptide having an amino acid sequence that is not substantially identical to an IMI polypeptide, e.g., a polypeptide that is not an IMI isoenzyme, which peptide performs a different function than an IMI polypeptide. Within the fusion polypeptide, the term "operably linked" is intended to indicate that the IMI polypeptide and the non-IMI polypeptide are fused to each other so that both sequences fulfill the proposed function attributed to the sequence used. The non-IMI polypeptide can be fused to the N-terminus or C-terminus of the IMI polypeptide. For example, in one embodiment, the fusion polypeptide is a GST-IMI fusion polypeptide in which the IMI sequence is fused to the C-terminus of the GST sequence. Such fusion polypeptides can facilitate the purification of recombinant IMI polypeptides. In another embodiment, the fusion polypeptide is an IMI polypeptide containing a heterologous signal sequence at its N-terminus. In certain host cells (e.g., mammalian host cells), expression and/or secretion of an IMI polypeptide can be increased through use of a heterologous signal sequence.

An isolated nucleic acid molecule encoding an IMI polypeptide having sequence identity to a polypeptide encoded by a polynucleotide sequence of SEQ ID NO:1, SEQ ID NO:3 or SEQ ID NO:5 can be created by introducing one or more nucleotide substitutions, additions or deletions into a nucleotide sequence of SEQ ID NO:1, SEQ ID NO:3 or SEQ ID NO:5 such that one or more amino acid substitutions, additions or deletions are introduced into the encoded polypeptide. Mutations can be introduced into a sequence of SEQ ID NO:1, SEQ ID NO:3 or SEQ ID NO:5 by standard techniques, such as site-directed mutagenesis and PCR-mediated mutagenesis. Preferably, conservative amino acid substitutions are made at one or more predicted non-essential amino acid residues.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an IMI polypeptide is preferably replaced with another amino acid residue from the same side chain family. Alternatively, in another embodiment, mutations can be introduced randomly along all or part of an IMI coding sequence, such as by saturation mutagenesis, and the resultant mutants can be screened for an IMI activity described herein to identify mutants that retain IMI activity. Following mutagenesis of the sequence of SEQ ID NO:1, SEQ ID NO:3 or SEQ ID NO:5, the encoded polypeptide can be expressed recombinantly and the activity of the polypeptide can be determined by analyzing the imidazolinone resistance of a plant expressing the polypeptide as described in the Examples below.

To determine the percent sequence identity of two amino acid sequences, the sequences are aligned for optimal comparison purposes (e.g., gaps 19 can be introduced in the sequence of one polypeptide for optimal alignment with the other polypeptide). The amino acid residues at corresponding amino acid positions are then compared. When a position in one sequence is occupied by the same amino acid residue as the corresponding position in the other sequence, then the molecules are identical at that position. The same type of comparison can be made between two nucleic acid sequences. The percent sequence identity between the two sequences is a function of the number of identical positions shared by the sequences (i.e., percent sequence identity=numbers of identical positions/total numbers of positions×100). For the purposes of the invention, the percent sequence identity, between two nucleic acid or polypeptide sequences is determined using the Vector NTI 6.0 (PC) software package (InforMax, 7600 Wisconsin Ave., Bethesda, Md. 20814). A gap opening penalty of 15 and a gap extension penalty of 6.66 are used for determining the percent identity of two nucleic acids. A gap opening penalty of 10 and a gap extension penalty of 0.1 are used for determining the percent identity of two polypeptides. All other parameters are set at the default settings.

It is to be understood that for the purposes of determining sequence identity, when comparing a DNA sequence to an RNA sequence, a thymidine nucleotide is equivalent to a uracil nucleotide. Preferably, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence shown in SEQ ID NO:2, SEQ ID NO:4 or SEQ ID NO:6. In another embodiment, the isolated IMI polypeptides included in the present invention are at least about 50-60%, preferably at least about 60-70%, and more preferably at least about 70-75%, 75-80%, 80-85%, 85-90% or 90-95%, and most preferably at least about 96%, 97%, 98%, 99% or more identical to an entire amino acid sequence shown in SEQ ID NO:2, SEQ ID NO:4 or SEQ ID NO:6. Additionally, optimized IMI nucleic acids can be created. Preferably, an optimized IMI nucleic acid encodes an IMI polypeptide that modulates a plant's tolerance to imidazolinone herbicides, and more preferably increases a plant's tolerance to an imidazolinone herbicide upon its over-expression in the plant. As used herein, "optimized" refers to a nucleic acid that is genetically engineered to increase its expression in a given plant or animal. To provide plant optimized IMI nucleic acids, the DNA sequence of the gene can be modified to 1) comprise codons preferred by highly expressed plant genes; 2) comprise an A+T content in nucleotide base composition to that substantially found in plants; 3) form a plant initiation sequence, 4) eliminate sequences that cause destabilization, inappropriate polyadenylation, degradation and termination of RNA, or that form secondary structure hairpins or RNA splice sites. Increased expression of IMI nucleic acids in plants can be achieved by utilizing the distribution frequency of codon usage in plants in general or a particular plant. Methods for optimizing nucleic acid expression in plants can be found in EPA 0359472; EPA 0385962; PCT Application No. WO 91/16432; U.S. Pat. Nos. 5,380,831; 5,436,391; Perlack et at., 1991 Proc. Natl. Acad. Sci. USA 88:3324-3328; and Murray et at., 1989 Nucleic Acids Res. 17:477-498.

As used herein, "frequency of preferred codon usage" refers to the preference exhibited by a specific host cell in usage of nucleotide codons to specify a given amino acid. To determine the frequency of usage of a particular codon in a gene, the number of occurrences of that codon in the gene is divided by the total number of occurrences of all codons specifying the same amino acid in the gene. Similarly, the frequency of preferred codon usage exhibited by a host cell can be calculated by averaging frequency of preferred codon usage in a large number of genes expressed by the host cell. It is preferable that this analysis be limited to genes that are highly expressed by the host cell. The percent deviation of the frequency of preferred codon usage for a synthetic gene from that employed by a host cell is calculated first by determining the percent deviation of the frequency of usage of a single codon from that of the host cell followed by obtaining the average deviation over all codons. As defined herein, this calculation includes unique codons (i.e., ATG and TGG). In general terms, the overall average deviation of the codon usage of an optimized gene from that of a host cell is calculated using the equation $1A = \sum_{n=1}^{Z} X_n - Y_n X_n$ times 100 Z where $X_n$=frequency of usage for codon n in the host cell; $Y_n$=frequency of usage for codon n in the synthetic gene, n represents an individual codon that specifies an amino acid and the total number of codons is Z. The overall deviation of the frequency of codon usage, A, for all amino acids should preferably be less than about 25%, and more preferably less than about 10%.

Hence, an IMI nucleic acid can be optimized such that its distribution frequency of codon usage deviates, preferably, no more than 25% from that of highly expressed plant genes and, more preferably, no more than about 10%. In addition, consideration is given to the percentage G+C content of the degenerate third base (monocotyledons appear to favor G+C in this position, whereas dicotyledons do not). It is also recognized that the XCG (where X is A, T, C, or G) nucleotide is the least preferred codon in dicots whereas the XTA codon is avoided in both monocots and dicots. Optimized IMI nucleic acids of this invention also preferably have CG and TA doublet avoidance indices closely approximating those of the chosen host plant (i.e., *Triticum aestivum*). More preferably these indices deviate from that of the host by no more than about 10-15%.

In addition to the nucleic acid molecules encoding the IMI polypeptides described above, another aspect of the invention pertains to isolated nucleic acid molecules that are antisense thereto. Antisense polynucleotides are thought to inhibit gene expression of a target polynucleotide by specifically binding the target polynucleotide and interfering with transcription, splicing, transport, translation and/or stability of the target polynucleotide. Methods are described in the prior art for targeting the antisense polynucleotide to the chromosomal DNA, to a primary RNA transcript or to a processed mRNA. Preferably, the target regions include splice sites, translation initiation codons, translation termination codons, and other sequences within the open reading frame.

The term "antisense", for the purposes of the invention, refers to a nucleic acid comprising a polynucleotide that is sufficiently complementary to all or a portion of a gene, primary transcript or processed mRNA, so as to interfere with expression of the endogenous gene. "Complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. The term "antisense nucleic acid" includes single stranded RNA as well as double-stranded DNA expression cassettes that can be transcribed to produce an antisense RNA. "Active" antisense nucleic acids are antisense RNA molecules that are capable of selectively hybridizing with a primary transcript or mRNA encoding a polypeptide having at least 80% sequence identity with the polypeptide sequence of SEQ ID NO:2, SEQ ID NO:4 or SEQ ID NO:6.

In addition to the IMI nucleic acids and polypeptides described above, the present invention encompasses these nucleic acids and polypeptides attached to a moiety. These moieties include, but are not limited to, detection moieties, hybridization moieties, purification moieties, delivery moieties, reaction moieties, binding moieties, and the like. A typical group of nucleic acids having moieties attached are probes and primers. Probes and primers typically comprise a substantially isolated oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of the sequence set forth in SEQ ID NO:1, SEQ ID NO:3 or SEQ ID NO:5, an anti-sense sequence of the sequence set forth in SEQ ID NO:1, SEQ ID NO:3 or SEQ ID NO:5, or naturally occurring mutants thereof. Primers based on a nucleotide sequence of SEQ ID NO:1, SEQ ID NO:3 or SEQ ID NO:5 can be used in PCR reactions to clone IMI homologs. Probes based on the IMI nucleotide sequences can be used to detect transcripts or genomic sequences encoding the same or homologous polypeptides. In preferred embodiments, the probe further comprises a label group attached thereto, e.g. the label group can be a radioisotope, a fluorescent compound, an enzyme, or an enzyme co-factor. Such probes can be used as a part of a genomic marker test kit for identifying cells which express an IMI polypeptide, such as by measuring a level of an IMI-encoding nucleic acid, in a sample of cells, e.g., detecting IMI mRNA levels or determining whether a genomic IMI gene has been mutated or deleted.

The invention further provides an isolated recombinant expression vector comprising an IMI nucleic acid as described above, wherein expression of the vector in a host cell results in increased resistance to an imidazolinone herbicide as compared to a wild type variety of the host cell. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operably linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel, Gene Expression Technology: Methods in Enzymology 185, Academic Press, San Diego, Calif. (1990) or see: Gruber and Crosby, in: Methods in Plant Molecular Biology and Biotechnology, eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of polypeptide desired, etc. The expression vectors of the invention can be introduced into host cells to thereby produce polypeptides or peptides, including fusion polypeptides or peptides, encoded by nucleic acids as described herein (e.g., IMI polypeptides, fusion polypeptides, etc.).

In a preferred embodiment of the present invention, the IMI polypeptides are expressed in plants and plants cells such as unicellular plant cells (such as algae) (see Falciatore et al., 1999 Marine Biotechnology 1(3):239-251 and references therein) and plant cells from higher plants (e.g., the spermatophytes, such as crop plants). An IMI polynucleotide may be "introduced" into a plant cell by any means, including transfection, transformation or transduction, electroporation, particle bombardment, agroinfection, biolistics and the like.

Suitable methods for transforming or transfecting host cells including plant cells can be found in Sambrook, et al. (Molecular Cloning: A Laboratory Manual. $2^{nd}$, ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, ed: Gartland and Davey, Humana Press, Totowa, N.J. As increased resistance to imidazolinone herbicides is a general trait wished to be inherited into a wide variety of plants like maize, wheat, rye, oat, triticale, rice, barley, soybean, peanut, cotton, rapeseed and canola, *manihot*, pepper, sunflower and *tagetes*, solanaceous plants like potato, tobacco, eggplant, and tomato, *Vicia* species, pea, alfalfa, bushy plants (coffee, cacao, tea), *Salix* species, trees (oil palm, coconut), perennial grasses and forage crops, these crop plants are also preferred target plants for a genetic engineering as one further embodiment of the present invention. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover.

In one embodiment of the present invention, transfection of an IMI polynucleotide into a plant is achieved by *Agrobacterium* mediated gene transfer. One transformation method known to those of skill in the art is the dipping of a flowering plant into an Agrobacteria solution, wherein the Agrobacteria contains the IMI nucleic acid, followed by breeding of the transformed gametes. *Agrobacterium* mediated plant transformation can be performed using for example the GV3101(pMP90) (Koncz and Schell, 1986 Mol. Gen. Genet. 204:383-396) or LBA4404 (Clontech) *Agrobacterium tumefaciens* strain. Transformation can be performed by standard transformation and regeneration techniques (Deblaere et al., 1994 Nucl. Acids. Res. 13:4777-4788; Gelvin, Stanton B. and Schilperoort, Robert A, Plant Molecular Biology Manual, $2^{nd}$ Ed.—Dordrecht: Kluwer Academic Publ., 1995.—in Sect., Ringbuc Zentrale Signatur: BTI 1-P ISBN 0-7923-2731-4; Glick, Bernard R. and Thompson, John E., Methods in Plant Molecular Biology and Biotechnology, Boca Raton: CRC Press, 1993 360 S., ISBN 0-8493-5164-2). For example, rapeseed can be transformed via cotyledon or hypocotyl transformation (Moloney et al., 1989 Plant cell Report 8:238-242; De Block et al., 1989 Plant Physiol. 91:694-701). Use of *antibiotica* for *Agrobacterium* and plant selection depends on the binary vector and the *Agrobacterium* strain used for transformation. Rapeseed selection is normally performed using kanamycin as selectable plant marker. *Agrobacterium* mediated gene transfer to flax can be performed using, for example, a technique described by Mlynarova et al., 1994 Plant Cell Report 13:282-285. Additionally, transformation of soybean can be performed using for example a technique described in European Patent No. 0424 047, U.S. Pat. No. 5,322,783, European Patent No. 0397 687, U.S. Pat. No. 5,376,543 or U.S. Pat. No. 5,169,770. Transformation of maize can be achieved by particle bombardment, polyethylene glycol mediated DNA uptake or via the silicon carbide fiber technique. (See, for example, Freeling and Walbot "The maize handbook" Springer Verlag: New York (1993) ISBN 3-540-97826-7). A specific example of maize transformation is found in U.S. Pat. No. 5,990,387 and a specific example of wheat transformation can be found in PCT Application No. WO 93/07256.

According to the present invention, the introduced IMI polynucleotide may be maintained in the plant cell stably if it is incorporated into a non-chromosomal autonomous replicon or integrated into the plant chromosomes. Alternatively, the introduced IMI polynucleotide may be present on an extra-chromosomal non-replicating vector and be transiently expressed or transiently active. In one embodiment, a homologous recombinant microorganism can be created wherein the IMI polynucleotide is integrated into a chromosome, a vector is prepared which contains at least a portion of an AHAS gene into which a deletion, addition or substitution has been introduced to thereby alter, e.g., functionally disrupt, the endogenous AHAS gene and to create an IMI gene. To create a point mutation via homologous recombination, DNA-RNA hybrids can be used in a technique known as chimeraplasty (Cole-Strauss et al., 1999 Nucleic Acids Research 27(5):1323-1330 and Kmiec, 1999 Gene therapy American Scientist 87(3):240-247). Other homologous recombination procedures in *Triticum* species are also well known in the art and are contemplated for use herein.

In the homologous recombination vector, the IMI gene can be flanked at its 5' and 3' ends by an additional nucleic acid molecule of the AHAS gene to allow for homologous recombination to occur between the exogenous IMI gene carried by the vector and an endogenous AHAS gene, in a microorganism or plant. The additional flanking AHAS nucleic acid molecule is of sufficient length for successful homologous recombination with the endogenous gene. Typically, several hundreds of base pairs up to kilobases of flanking DNA (both at the 5' and 3' ends) are included in the vector (see e.g., Thomas, K. R., and Capecchi, M. R., 1987 Cell 51:503 for a description of homologous recombination vectors or Strepp et al., 1998 PNAS, 95(8):4368-4373 for cDNA based recombination in *Physcomitrella patens*). However, since the IMI gene normally differs from the AHAS gene at very few amino acids, a flanking sequence is not always necessary. The homologous recombination vector is introduced into a microorganism or plant cell (e.g., via polyethylene glycol mediated DNA), and cells in which the introduced IMI gene has homologously recombined with the endogenous AHAS gene are selected using art-known techniques.

In another embodiment, recombinant microorganisms can be produced that contain selected systems that allow for regulated expression of the introduced gene. For example, inclusion of an IMI gene on a vector placing it under control of the lac operon permits expression of the IMI gene only in the presence of IPTG. Such regulatory systems are well known in the art.

Whether present in an extra-chromosomal non-replicating vector or a vector that is integrated into a chromosome, the IMI polpucleotide preferably resides in a plant expression cassette. A plant expression cassette preferably contains regulatory sequences capable of driving gene expression in plant cells that are operably linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984 EMBO J. 3:835) or functional equivalents thereof, but also all other terminators functionally active in plants are suitable. As plant gene expression is very often not limited on transcriptional levels, a plant expression cassette preferably contains other operably linked sequences like translational enhancers such as the overdrive-sequence containing the 5'-untranslated leader sequence from tobacco mosaic virus enhancing the polypeptide per RNA ratio (Gallie et al., 1987 Nucl. Acids Research 15:8693-8711). Examples of plant expression vectors include those detailed in: Becker, D. et al., 1992 New plant binary vectors with selectable markers located proximal to the left border, Plant Mol. Biol. 20:1195-1197; Bevan, M. W., 1984 Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operably linked to an appropriate promoter conferring gene expression in a timely, cell or tissue specific manner. Promoters useful in the expression cassettes of the invention include any promoter that is capable of initiating transcription in a plant cell. Such promoters include, but are not limited to those that can be obtained from plants, plant viruses and bacteria that contain genes that are expressed in plants, such as *Agrobacterium* and *Rhizobium*.

The promoter may be constitutive, inducible, developmental stage-preferred, cell type-preferred, tissue-preferred or organ-preferred. Constitutive promoters are active under most conditions. Examples of constitutive promoters include the CaMV 19S and 35S promoters (Odell et al. 1985 Nature 313:810-812), the sX CaMV 35S promoter (Kay et al. 1987 Science 236:1299-1302) the Sep 1 promoter, the rice actin promoter (McElroy et al. 1990 Plant Cell 2:163-171), the *Arabidopsis* actin promoter, the ubiquitan promoter (Christensen et al. 1989 Plant Molec Biol. 18:675-689); pEmu (Last et al. 1991 Theor Appl Genet. 81:581-588), the figwort mosaic virus 35S promoter, the Smas promoter (Velten et al. 1984 EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like.

Inducible promoters are active under certain environmental conditions, such as the presence or absence of a nutrient or metabolite, heat or cold, light, pathogen attack, anaerobic conditions, and the like. For example, the hsp80 promoter from *Brassica* is induced by heat shock, the PPDK promoter is induced by light, the PR-1 promoter from tobacco, *Arabidopsis* and maize are inducible by infection with a pathogen, and the Adh1 promoter is induced by hypoxia and cold stress. Plant gene expression can also be facilitated via an inducible promoter (for review see Gatz, 1997 Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1992 Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al., 1989 BioEssays 10:108. Examples of seed preferred promoters include, but are not limited to cellulose synthase (cel A), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al., 1991 Mot Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980) or the legumin B4 promoter (LeB4; Baeumlein et al., 1992 Plant Journal, 2(2):233-9) as well as promoters conferring seed specific expression in monocot plants like maize, barley, wheat, rye, rice, etc. Suitable promoters to note are the 1pt2 or 1pt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, Sorghum kasirin-gene and rye secalin gene).

Other promoters useful in the expression cassettes of the invention include, but are not limited to, the major chlorophyll a/b binding protein promoter, histone promoters, the Ap3 promoter, the conglycin promoter, the napin promoter, the soy bean lectin promoter, the maize 15 kD zein promoter, the 22 kD zein promoter, the 27KD zein promoter, the g-zein promoter, the waxy, shrunken 1, shrunken 2 and bronze promoters, the Zm13 promoter (U.S. Pat. No. 5,086,169), the maize polygalacturonase promoters (PG) (U.S. Pat. Nos. 5,412,085 and 5,545,546) and the SGB6 promoter (U.S. Pat. No. 5,470,359), as well as synthetic or other natural promoters.

Additional flexibility in controlling heterologous gene expression in plants may be obtained by using DNA binding domains and response elements from heterologous sources (i.e., DNA binding domains from non-plant sources). An example of such a heterologous DNA binding domain is the LexA DNA binding domain (Brent and Ptashne, 1985 Cell 43:729-736).

Another aspect of the invention pertains to host cells into which a recombinant expression vector of the invention has been introduced. The terms "host cell" and "recombinant host cell" are used interchangeably herein. It is understood that such terms refer not only to the particular subject cell but they also apply to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, an IMI polynucleotide can be expressed in bacterial cells such as *C. glutamicum*, insect cells, fungal cells or mammalian cells (such as Chinese hamster ovary cells (CHO) or COS cells), algae, ciliates, plant cells, fungi or other microorganisms like *C. glutamicum*. Other suitable host cells are known to those skilled in the art.

A host cell of the invention, such as a prokaryotic or eukaryotic host cell in culture, can be used to produce (i.e., express) an IMI polynucleotide. Accordingly, the invention further provides methods for producing IMI polypeptides using the host cells of the invention. In one embodiment, the method comprises culturing the host cell of invention (into which a recombinant expression vector encoding an IMI polypeptide has been introduced, or into which genome has been introduced a gene encoding a wild-type or IMI polypeptide) in a suitable medium until IMI polypeptide is produced. In another embodiment, the method further comprises isolating IMI polypeptides from the medium or the host cell. Another aspect of the invention pertains to isolated IMI polypeptides, and biologically active portions thereof. An "isolated" or "purified" polypeptide or biologically active portion thereof is free of some of the cellular material when produced by recombinant DNA techniques, or chemical precursors or other chemicals when chemically synthesized. The language "substantially free of cellular material" includes preparations of IMI polypeptide in which the polypeptide is separated from some of the cellular components of the cells in which it is naturally or recombinantly produced. In one embodiment, the language "substantially free of cellular material" includes preparations of an IMI polypeptide having less than about 30% (by dry weight) of non-IMI material (also referred to herein as a "contaminating polypeptide"), more preferably less than about 20% of non-IMI material, still more preferably less than about 10% of non-IMI material, and most preferably less than about 5% non-IMI material.

When the IMI polypeptide, or biologically active portion thereof, is recombinantly produced, it is also preferably substantially free of culture medium, i.e., culture medium represents less than about 20%, more preferably less than about 10%, and most preferably less than about 5% of the volume of the polypeptide preparation. The language "substantially free of chemical precursors or other chemicals" includes preparations of IMI polypeptide in which the polypeptide is separated from chemical precursors or other chemicals that are involved in the synthesis of the polypeptide. In one embodiment, the language "substantially free of chemical precursors or other chemicals" includes preparations of an IMI polypeptide having less than about 30% (by dry weight) of chemical precursors or non-IMI chemicals, more preferably less than about 20% chemical precursors or non-IMI chemicals, still more preferably less than about 10% chemical precursors or non-IMI chemicals, and most preferably less than about 5% chemical precursors or non-IMI chemicals. In preferred embodiments, isolated polypeptides, or biologically active portions thereof, lack contaminating polypeptides from the same organism from which the IMI polypeptide is derived. Typically, such polypeptides are produced by recombinant expression of, for example, a *Triticum aestivum* IMI polypeptide in plants other than *Triticum aestivum* or microorganisms such as *C. glutamicum*, ciliates, algae or fungi.

The IMI polynucleotide and polypeptide sequences of the invention have a variety of uses. The nucleic acid and amino acid sequences of the present invention can be used to transform plants, thereby modulating the plant's resistance to imidazolinone herbicides. Accordingly, the invention provides a method of producing a transgenic plant having increased tolerance to an imidazolinone herbicide comprising, (a) transforming a plant cell with one or more expression vectors comprising one or more IMI nucleic acids, and (b) generating from the plant cell a transgenic plant with an increased resistance to an imidazolinone herbicide as compared to a wild type variety of the plant. In one embodiment, the multiple IMI nucleic acids are derived from different genomes. Also included in the present invention are methods of producing a transgenic plant having increased tolerance to an imidazolinone herbicide comprising, (a) transforming a plant cell with an expression vector comprising an IMI nucleic acid, wherein the nucleic acid is a non-Imi1 nucleic acid and (b) generating from the plant cell a transgenic plant with an increased resistance to an imidazolinone herbicide as compared to a wild type variety of the plant.

The present invention includes methods of modifying a plant's tolerance to an imidazolinone herbicide comprising modifying the expression of one or more IMI nucleic acids. Preferably, the nucleic acids are located on or derived from different genomes. The plant's resistance to the imidazolinone herbicide can be increased or decreased as achieved by increasing or decreasing the expression of an IMI polynucleotide, respectively. Preferably, the plant's resistance to the imidazolinone herbicide is increased by increasing expression of an IMI polynucleotide. Expression of an IMI polynucleotide can be modified by any method known to those of skill in the art. The methods of increasing expression of IMI polynucleotides can be used wherein the plant is either transgenic or not transgenic. In cases when the plant is transgenic, the plant can be transformed with a vector containing any of the above described IMI coding nucleic acids, or the plant can be transformed with a promoter that directs expression of endogenous IMI polynucleotides in the plant, for example. The invention provides that such a promoter can be tissue specific or developmentally regulated. Alternatively, non-transgenic plants can have endogenous IMI polynucleotide expression modified by inducing a native promoter. The expression of polynucleotides comprising SEQ ID NO:1, SEQ ID NO:3 or SEQ ID NO:5 in target plants can be accomplished by, but is not limited to, one of the following examples: (a) constitutive promoter, (b) chemical-induced promoter, and (c) engineered promoter over-expression with for example zinc-finger derived transcription factors (Greisman and Pabo, 1997 Science 275: 657).

In a preferred embodiment, transcription of the IMI polynucleotide is modulated using zinc-finger derived transcription factors (ZFPs) as described in Greisman and Pabo, 1997 Science 275:657 and manufactured by Sangamo Biosciences, Inc. These ZFPs comprise both a DNA recognition domain and a functional domain that causes activation or repression of a target nucleic acid such as an IMI nucleic acid. Therefore, activating and repressing ZFPs can be created that specifically recognize the IMI polynucleotide promoters described above and used to increase or decrease IMI polynucleotide expression in a plant, thereby modulating the herbicide resistance of the plant.

As described in more detail above, the plants produced by the methods of the present invention can be monocots or dicots. The plants can be selected from maize, wheat, rye, oat, triticale, rice, barley, soybean, peanut, cotton, rapeseed, canola, *manihot*, pepper, sunflower, *tagetes*, solanaceous plants, potato, tobacco, eggplant, tomato, *Vicia* species, pea, alfalfa, coffee, cacao, tea, Salix species, oil palm, coconut, perennial grass and forage crops, for example. In a preferred embodiment, the plant is a wheat plant. Forage crops include, but are not limited to, Wheatgrass, Canarygrass, Bromegrass, Wildrye Grass, Bluegrass, Orchardgrass, Alfalfa, Salfoin, Birdsfoot Trefoil, Alsike Clover, Red Clover and Sweet Clover. In a preferred embodiment, the plant is a wheat plant. In each of the methods described above, the plant cell includes, but is not limited to, a protoplast, gamete producing cell, and a cell that regenerates into a whole plant. As used herein, the term "transgenic" refers to any plant, plant cell, callus, plant tissue or plant part, that contains all or part of at least one recombinant polynucleotide. In many cases, all or part of the recombinant polynucleotide is stably integrated into a chromosome or stable extra-chromosomal element, so that it is passed on to successive generations.

As described above, the present invention teaches compositions and methods for increasing the imidazolinone resistance of a wheat plant or seed as compared to a wild-type variety of the plant or seed. In a preferred embodiment, the imidazolinone resistance of a wheat plant or seed is increased such that the plant or seed can withstand an imidazolinone herbicide application of preferably approximately 10-400 g ai ha$^{-1}$, more preferably 20-160 g ai ha$^{-1}$, and most preferably 40-80 g ai ha$^{-1}$. As used herein, to "withstand" an imidazolinone herbicide application means that the plant is either not killed or not injured by such application.

Additionally provided herein is a method of controlling weeds within the vicinity of a wheat plant, comprising applying an imidazolinone herbicide to the weeds and to the wheat plant, wherein the wheat plant has increased resistance to the imidazolinone herbicide as compared to a wild type variety of the wheat plant, and wherein the plant comprises one or more IMI nucleic acids. In one embodiment, the plant comprises multiple IMI nucleic acids located on or derived from different genomes. In another embodiment, the plant comprises a non-Imi1 nucleic acid. By providing for wheat plants having increased resistance to imidazolinone, a wide variety of formulations can be employed for protecting wheat plants from weeds, so as to enhance plant growth and reduce competition for nutrients. An imidazolinone herbicide can be used by itself for pre-emergence, post-emergence, pre-planting and at-planting control of weeds in areas surrounding the wheat plants described herein or an imidazolinone herbicide formulation can be used that contains other additives. The imidazolinone herbicide can also be used as a seed treatment. Additives found in an imidazolinone herbicide formulation include other herbicides, detergents, adjuvants, spreading agents, sticking agents, stabilizing agents, or the like. The imidazolinone herbicide formulation can be a wet or dry preparation and can include, but is not limited to, flowable powders, emulsifiable concentrates and liquid concentrates. The imidazolinone herbicide and herbicide formulations can be applied in accordance with conventional methods, for example, by spraying, irrigation, dusting, or the like.

Throughout this application, various publications are referenced. The disclosures of all of these publications and those references cited within those publications in their entireties are hereby incorporated by reference into this application in order to more fully describe the state of the art to which this invention pertains.

It should also be understood that the foregoing relates to preferred embodiments of the present invention and that numerous changes may be made therein without departing from the scope of the invention. The invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention and/or the scope of the appended claims.

EXAMPLES

Example 1

Mutagenesis and Selection of Resistant Gunner Wheat Lines

The imidazolinone resistant wheat was derived through mutation and conventional selection and breeding. Initial seed mutagenesis was conducted as follows:

1. Seeds of the hard red spring wheat variety Gunner, were pre-soaked in tap water.

2. After decanting the tap water, a solution of 0.03% Ethylmethane sulfonate (EMS) and 0.02% Diethyl Sulfate (DES) was poured in to the seed container. The container was shaken every 10-15 minutes during the course of a two-hour treatment.

3. The EMS and DES solution was decanted and a solution of 0.02% sodium azide in 0.001 M phosphate buffer was added.

4. Step three was repeated.

5. Seeds were then rinsed in tap water and dried. After drying, seeds were planted.

6. Planted seeds represented the M1 generation. Seed harvested from M1 plants represented the M2 generation.

M2 seed were planted and emerged plants were treated with imazamox herbicide at approximately the 2-3 leaf stage at rates which would kill susceptible wheat. A total of nine herbicide tolerant plants were selected and re-planted in a greenhouse. Progeny seed were collected from each of the nine plants. This seed was planted in a greenhouse. Plants were sprayed with imazamox herbicide at 80 g. a.i./ha.+1.0% Sun-It adjuvant (v/v) and evaluated for tolerance. A total of twelve plants of two lines, designated HRS198205 and HRS198208, were identified as most tolerant. Segregation for herbicide tolerance in each line was consistent with a single semi-dominant gene. Progeny seed of the 24 plants were collected and re-planted in a greenhouse for further evaluation and selection. Plants were sprayed with imazamox herbicide at 80 g. a.i./ha.+1.0% Sun-It adjuvant (v/v) resulting in the identification of sub-lines that exhibited the highest level of tolerance. In addition, the sub-lines were determined to have the phenotypic characteristics of Gunner.

Progeny seed of HRS 198205 and HRS198208 were collected and planted in the field. Field plots were sprayed with imazamox herbicide at 80 g. a.i./ha.+1.0% Sun-It adjuvant (v/v). All plants in each line exhibited the same level of acceptable tolerance to imazamox herbicide. Based upon these results, seed harvested from plots of five of the HRS 198205 sub-lines were combined into a single lot that was designated AP205CL (referred to above as Gunner IMI 205). Additionally, seed harvested from plots of five of the HRS198208 sub-lines were combined into a single lot that was designated AP602CL (referred to above as Gunner IMI 208). Seed increases were conducted at several locations. All seed increases were sprayed with imazamox herbicide at 40 g. a.i./ha+0.25% (v/v) non-ionic surfactant. No herbicide susceptible plants were observed. In addition, all plants were comparable to plants of the variety Gunner.

Example 2

Mutagenesis and Selection of Resistant Madsen Wheat Lines

Seeds of the soft white winter wheat variety Madsen, were pre-soaked in tap water. After decanting the tap water, a solution of 0.03% EMS and 0.02% DES was poured into the seed container. The container was shaken every 10-15 minutes during the course of a two-hour treatment. The EMS and DES solution was decanted and a solution of 0.02% sodium azide in 0.001 M phosphate buffer was added. The container again was shaken every 10-15 minutes during the course of a two-hour treatment. Seeds were then rinsed in tap water and dried. After drying, seeds were planted. Planted seeds represented the $M_1$ generation. $M_1$ plants were allowed to self-pollinate and the M2 seed harvested as a bulk. Approximately 0.2 hectares of M2 seed were planted in the field and resultant plants treated with an imazamox rate of 40 g. ai/ha. Twelve M2 plants were identified as tolerant. These plants were dug, and sent to Pullman, Wash. for vernalization and M3 seed production. M3 seed from each of the M2 plants were planted in the greenhouse and resultant plants were vernalized for 8 weeks, then treated with 80 g. ai/ha of Imazamox. Plants were selected based upon observed levels of tolerance and repotted for seed production. The M2:3 line designated Madsen1 selected as tolerant to 40 g/ha imazamox as an M2 was confirmed as tolerant to imazamox at the 80 g/ha rate applied to M3 progeny. Subsequent molecular characterization determined that Madsen1 had a mutation in the Als2 AHAS gene known to confer tolerance to imidazolinone herbicides.

Example 3

Tolerance of the AP205CL and AP602CL Wheat Plants to Imidazolinone Herbicides

Both the AP205CL and AP602CL wheat plants are tolerant to imidazolinone herbicides due to a mutation of the AHAS enzyme that is resistant to inhibition by these herbicides in vitro. This is demonstrated by comparison of the activity of the AHAS enzyme extracted from wild type wheat to the AHAS activity extracted from herbicide tolerant AP205CL plants (FIG. 2A) and AP602CL plants (FIG. 2B). The values in FIG. 1 are expressed as a percent of uninhibited activity. The AHAS enzyme from wild type Gunner wheat exhibits a 1 to 35 percent reduction of activity in the presence of a low concentration (1 M) of imidazolinone herbicide imazamox. This activity continues to decline to nearly 100 percent inhibition of the enzyme at higher herbicide concentrations (100 M). In contrast, the AHAS enzyme extracted from herbicide tolerant AP205CL plants retains nearly 90 percent of its activity at the 1 M imazamox concentration, and approximately one third of its activity at the higher (50 M to 100 M) concentrations. The AHAS enzyme extracted from herbicide tolerant AP602CL plants retains nearly 80-100 percent of its activity at the 1 M imazamox concentration, and nearly half of its activity at the higher (50 M to 100 M) concentrations. These levels of activity are sufficient to allow the tolerant wheat plants to survive the application of imazamox, as was observed during the selection process (Example 1).

Example 4

Tolerance of the Madsen Wheat Plants to Imidazolinone Herbicides

Madsen1 was evaluated for tolerance to the imidazolinone herbicide imazamox at 40 and 80 g/ha in a greenhouse trial. The susceptible wheat cultivar Teal was used as a control. Evaluation was made 14 days after treatment. Injury was scored on a 0-9 scale, 0 representing no injury and 9 representing plant death. The data presented in FIG. 3 demonstrate that Madsen1 has tolerance to imazamox.

Because the tolerance in Madsen1 is due to a mutation in the AHAS enzyme rendering it resistant to inhibition by imidazolinone herbicides, the in vitro activity of AHAS extracted from wild type plants (not having the mutation for tolerance) can be compared to the in vitro activity of AHAS extracted from tolerant plants in the presence of varying concentrations of an imidazolinone (IMI) herbicide. Madsen1 was compared to the wild type variety Madsen. The results are shown in FIG. 3. FIG. 3 shows that as the concentration of imazamox increased, the uninhibited AHAS enzyme activity decreased faster in wild type lines than in Madsen). At 100 μM imazamox, the residual uninhibited AHAS is sufficient to provide a herbicide tolerant response in Madsen1.

Example 4

Feedback Inhibition of AHAS Enzyme Activity by Leucine and Valine

AHAS is known to be feedback inhibited by the branched chain amino acids. Valine and leucine in combination are especially effective inhibitors. When examined, AHAS enzymes extracted from the wild-type variety Gunner, AP205CL and AP602CL all exhibited comparable patterns of inhibition by the combination of valine and leucine (FIGS. 4A and 4B).

---

What is claimed is:

1. A *Triticum aestivum* wheat plant comprising:
   (a) multiple *Triticum* Imi nucleic acids from different genomes,
      (i) a first of the multiple Imi nucleic acids being a B-genome Imi2 nucleic acid which, as a result of random mutagenesis, encodes an IMI2 polypeptide having a serine to asparagine substitution in Domain E as compared to a wild-type AHAS polypeptide, wherein the Imi2 nucleic acid encodes the IMI2 polypeptide of one of:
         (a) a plant of line Madsen M1, a representative sample of seed of the line having been deposited with ATCC under Patent Deposit Designation Number PTA-4255, wherein the IMI2 polypeptide of the plant of the line Madsen M1 comprises the serine to asparagine substitution in Domain E; or
         (b) a plant of line Gunner 208, a representative sample of seed of the line having been deposited with ATCC under Patent Deposit Designation Number PTA-4214, wherein the plant of the line Gunner 208 comprises the serine to asparagine substitution in Domain E, and
      (ii) a second of the multiple Imi nucleic acids being a D-genome Imi1 nucleic acid which, as a result of random mutagenesis, encodes an Imi1 polypeptide having a serine to asparagine substitution in Domain E as compared to a wild-type AHAS polypeptide,
      wherein the Imi1 nucleic acid encodes the Imi1 polypeptide of one of:
         (I) a plant of line Gunner 205, a representative sample of seed of the line having been deposited with ATCC under Patent Deposit Designation Number PTA-4213, wherein the Imi1 polypeptide of the plant of line Gunner 205 comprises the serine to asparagine substitution in Domain E; or
         (I) a plant of line FS-4, wherein the Imi1 polypeptide of the plant of the line FS-4 comprises the serine to asparagine substitution in Domain E; and
   (b) a phenotype of increased tolerance to an AHAS inhibitor herbicide relative to that of a wild-type variety of the plant,
   wherein said phenotype comprises (A) tolerance to 80 g a.i./ha imidazolinone herbicide, and (B) phytotoxicity less than 3.3 of 9 when the plant is treated with 40 g a.i./ha imazamox herbicide.

2. The wheat plant of claim 1, wherein the wheat plant is a non-transgenic, non-genetically engineered wheat plant.

3. The wheat plant of claim 1, wherein the wheat plant is winter wheat plant.

4. The wheat plant of claim 3, wherein the winter wheat plant is a derivative of a plant of line Madsen M1 a representative sample of seed of said plant having been deposited in the American Type Culture Collection under Accession No. PTA-4255.

5. A plant part, cell, or seed of the plant of claim 1, wherein said plant part, cell, or seed comprises said multiple Imi nucleic acids.

6. The seed of claim 5, wherein said seed further comprises a seed treatment.

7. The seed of claim 6, wherein the seed treatment comprises an AHAS-inhibiting herbicide.

8. The seed of claim 7, wherein the AHAS-inhibiting herbicide comprises an imidazolinone herbicide.

9. The seed of claim 8, wherein the imidazolinone herbicide comprises at least one of:
   imazapyr, imazethapyr, imazapic, imazamox, imazaquin, or imazethabenz.

10. A method for controlling weeds within the vicinity of a wheat plant, comprising:
    (a) providing the treated seed of claim 6; and
    (b) growing a wheat plant from said seed;
    thereby controlling the weeds in the vicinity thereof.

11. A method for controlling weeds within the vicinity of a wheat plant, comprising:
    (a) growing, the wheat plant of claim 1; and
    (b) contacting said plant and weeds in the vicinity thereof with an effective amount of an AHAS-inhibiting herbicide to which the plant is tolerant;
    thereby controlling the weeds.

12. The method of claim 11, wherein said AHAS-inhibiting herbicide comprises an imidazolinone herbicide.

13. The method of claim 12, wherein said imidazolinone herbicide comprises at least one of: imazapyr, imazethapyr, imazapic, imazamox, imazaquin, or imazethabenz.

14. A method for identifying the presence of an Imi2 nucleic acid in a plant, plant part, cell or seed thereof, comprising:
    (a) providing a plant, plant part, cell, or seed of claim 5;
    (b) extracting nucleic acid material from said plant, plant part, cell, or seed;
    (c) assaying the extracted nucleic acid material for the presence of the Imi2 nucleic acid.

15. The method of claim 14, wherein said assaying step (c) comprises a probe directed to said Imi2 nucleic acid.

16. The method of claim 11, wherein the AHAS-inhibiting herbicide comprises at least one of other herbicides, detergents, adjuvants, spreading agents, sticking agents or stabilizing agents.

17. The method of claim 11, wherein the AHAS-inhibiting herbicide is a flowable powder, an emulsifiable concentrate or a liquid concentrate.

\* \* \* \* \*

SEQUENCE LISTING

<160> NUMBER OF SEQ ID NOS: 11

<210> SEQ ID NO 1
<211> LENGTH: 411
<212> TYPE: DNA
<213> ORGANISM: Triticum aestivum

<400> SEQUENCE: 1

```
tgctgtggcc aacccaggtg ttacagttgt tgacattgat ggtgatggta gtttcctcat      60
gaacattcag gagttggcgt tgatccgcat tgagaacctc ccagtgaagg tgatgatatt     120
gaacaaccag catctgggaa tggtggtgca gtgggaggat aggttttaca aggccaatcg     180
```

```
ggcgcacaca taccttggca acccagaaaa tgagagtgag atatatccag attttgtgac      240
gattgctaaa ggattcaacg ttccagcagt tcgagtgacg aagaagagcg aagtcactgc      300
agcaatcaag aagatgcttg agaccccagg gccatacttg ttggatatca tagtcccgca      360
tcaggagcac gtgctgccta tgatcccaaa cggtggtgct ttcaaggaca t              411
```

```
<210> SEQ ID NO 2
<211> LENGTH: 168
<212> TYPE: PRT
<213> ORGANISM: Triticum aestivum

<400> SEQUENCE: 2

Ala Gln Tyr Tyr Thr Tyr Lys Arg Pro Arg Gln Trp Leu Ser Ser Ser
1               5                   10                  15

Gly Leu Gly Ala Met Gly Phe Gly Leu Pro Ala Ala Ala Gly Ala Ala
            20                  25                  30

Val Ala Asn Pro Gly Val Thr Val Asp Ile Asp Gly Asp Gly Ser
        35                  40                  45

Phe Leu Met Asn Ile Gln Glu Leu Ala Leu Ile Arg Ile Glu Asn Leu
    50                  55                  60

Pro Val Lys Val Met Ile Leu Asn Asn Gln His Leu Gly Met Val Val
65                  70                  75                  80

Gln Trp Glu Asp Arg Phe Tyr Lys Ala Asn Arg Ala His Thr Tyr Leu
                85                  90                  95

Gly Asn Pro Glu Asn Glu Ser Glu Ile Tyr Pro Asp Phe Val Thr Ile
            100                 105                 110

Ala Lys Gly Phe Asn Val Pro Ala Val Arg Val Thr Lys Lys Ser Glu
        115                 120                 125

Val Thr Ala Ala Ile Lys Lys Met Leu Glu Thr Pro Gly Pro Tyr Leu
    130                 135                 140

Leu Asp Ile Ile Val Pro His Gln Glu His Val Leu Pro Met Ile Pro
145                 150                 155                 160

Asn Gly Gly Ala Phe Lys Asp Met
                165
```

```
<210> SEQ ID NO 3
<211> LENGTH: 511
<212> TYPE: DNA
<213> ORGANISM: Triticum aestivum

<400> SEQUENCE: 3
gcggctcagt attacactta caagcggcca cggcagtggc tgtcttcatc cggtttgggt       60
gcaatgggat tgggttgcc agctgcagct ggcgctgctg tggccaaccc aggtgttaca      120
gttgttgaca ttgatgggga tggtagtttc ctcatgaaca ttcaggagtt ggcgttgatc      180
cgtattgaga acctcccagt gaaggtgatg atattgaaca accagcatct gggaatggtg      240
gtgcagtggg aggataggtt ttacaaggcc aacggcgc acacatacct tggcaaccca      300
gaaaatgaga gtgagatata tccagatttt gtgacgattg ctaaaggatt caacgttccg      360
gcagttcgtg tgacgaagaa gagcgaagtc actgcagcaa tcaagaagat gcttgagacc      420
ccagggccat acttgttgga tatcattgtc ccgcatcagg agcacgtgct gcctatgatc      480
ccaaacggtg gtgcttttaa ggacatgatc c                                    511
```

```
<210> SEQ ID NO 4
<211> LENGTH: 168
<212> TYPE: PRT
```

<213> ORGANISM: Triticum aestivum

<400> SEQUENCE: 4

```
Ala Gln Tyr Tyr Thr Tyr Lys Arg Pro Arg Gln Trp Leu Ser Ser Ser
1               5                   10                  15
Gly Leu Gly Ala Met Gly Phe Gly Leu Pro Ala Ala Gly Ala Ala
            20                  25                  30
Val Ala Asn Pro Gly Val Thr Val Asp Ile Asp Gly Asp Gly Ser
        35                  40                  45
Phe Leu Met Asn Ile Gln Glu Leu Ala Leu Ile Arg Ile Glu Asn Leu
    50                  55                  60
Pro Val Lys Val Met Ile Leu Asn Asn Gln His Leu Gly Met Val Val
65                  70                  75                  80
Gln Trp Glu Asp Arg Phe Tyr Lys Ala Asn Arg Ala His Thr Tyr Leu
                85                  90                  95
Gly Asn Pro Glu Asn Glu Ser Glu Ile Tyr Pro Asp Phe Val Thr Ile
            100                 105                 110
Ala Lys Gly Phe Asn Val Pro Ala Val Arg Val Thr Lys Lys Ser Glu
        115                 120                 125
Val Thr Ala Ala Ile Lys Lys Met Leu Glu Thr Pro Gly Pro Tyr Leu
    130                 135                 140
Leu Asp Ile Ile Val Pro His Gln Glu His Val Leu Pro Met Ile Pro
145                 150                 155                 160
Asn Gly Gly Ala Phe Lys Asp Met
                165
```

<210> SEQ ID NO 5
<211> LENGTH: 498
<212> TYPE: DNA
<213> ORGANISM: Triticum aestivum

<400> SEQUENCE: 5

```
ggctcagtat tacacttaca agcggccacg gcagtggctg tcttcatccg gtttgggtgc      60
aatgggattt gggttgccag ctgcagctgg cgctgctgtg ccaacccag gtgttacagt      120
tgttgacatt gatggggatg gtagtttcct catgaacatt caggagttgg cgttgatccg      180
tattgagaac ctcccagtga aggtgatgat attgaacaac cagcatctgg gaatggtggt      240
gcagtgggag ataggtttt acaaggccaa ccgggcgcac acataccttg caacccaga      300
aaatgagagt gagatatatc cagattttgt gacgattgct aaaggattca acgttccggc      360
agttcgtgtg acgaagaaga gcgaagtcac tgcagcaatc aagaagatgc ttgagacccc      420
agggccatac ttgttggata tcattgtccc gcatcaggag cacgtgctgc ctatgatccc      480
aaacggtggt gcttttaa                                                    498
```

<210> SEQ ID NO 6
<211> LENGTH: 168
<212> TYPE: PRT
<213> ORGANISM: Triticum aestivum

<400> SEQUENCE: 6

```
Ala Gln Tyr Tyr Thr Tyr Lys Arg Pro Arg Gln Trp Leu Ser Ser Ser
1               5                   10                  15
Gly Leu Gly Ala Met Gly Phe Gly Leu Pro Ala Ala Gly Ala Ala
            20                  25                  30
Val Ala Asn Pro Gly Val Thr Val Asp Ile Asp Gly Asp Gly Ser
        35                  40                  45
```

```
Phe Leu Met Asn Ile Gln Glu Leu Ala Leu Ile Arg Ile Glu Asn Leu
        50                  55                  60
Pro Val Lys Val Met Ile Leu Asn Asn Gln His Leu Gly Met Val Val
 65                 70                  75                  80
Gln Trp Glu Asp Arg Phe Tyr Lys Ala Asn Arg Ala His Thr Tyr Leu
                85                  90                  95
Gly Asn Pro Glu Asn Glu Ser Glu Ile Tyr Pro Asp Phe Val Thr Ile
            100                 105                 110
Ala Lys Gly Phe Asn Val Pro Ala Val Arg Val Thr Lys Lys Ser Glu
        115                 120                 125
Val Thr Ala Ala Ile Lys Lys Met Leu Glu Thr Pro Gly Pro Tyr Leu
    130                 135                 140
Leu Asp Ile Ile Val Pro His Gln Glu His Val Leu Pro Met Ile Pro
145                 150                 155                 160
Asn Gly Gly Ala Phe Lys Asp Met
                165

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence:
      Illustrative conserved peptide

<400> SEQUENCE: 7

Ala Ile Thr Gly Gln Val Pro Arg Arg Met Ile Gly Thr
 1               5                   10

<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      Illustrative conserved peptide

<400> SEQUENCE: 8

Gln Trp Glu Asp
 1

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence:
      Illustrative conserved peptide

<400> SEQUENCE: 9

Val Phe Ala Tyr Pro Gly Gly Ala Ser Met Glu Ile His Gln Ala Leu
 1               5                   10                  15
Thr Arg Ser

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:
      Illustrative conserved peptide

<400> SEQUENCE: 10
```

```
Ala Phe Gln Glu Thr Pro
1               5

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence:
      Illustrative conserved peptide

<400> SEQUENCE: 11

Ile Pro Ser Gly Gly
1               5
```